US010130342B2

(12) United States Patent
Frinking et al.

(10) Patent No.: US 10,130,342 B2
(45) Date of Patent: Nov. 20, 2018

(54) INITIALIZATION OF FITTING PARAMETERS FOR PERFUSION ASSESSMENT BASED ON BOLUS ADMINISTRATION

(75) Inventors: Peter Frinking, Plan-les-Ouates (CH); Nicolas Rognin, Bothell, WA (US); Marcel Arditi, Plan-les-Ouates (CH)

(73) Assignee: Bracco Suisse SA, Manno (CH)

( * ) Notice: Subject to any disclaimer, the term of this patent is extended or adjusted under 35 U.S.C. 154(b) by 712 days.

(21) Appl. No.: 13/607,354

(22) Filed: Sep. 7, 2012

(65) Prior Publication Data
US 2013/0060135 A1   Mar. 7, 2013

Related U.S. Application Data

(63) Continuation-in-part of application No. PCT/EP2011/053460, filed on Mar. 8, 2011, and a
(Continued)

(30) Foreign Application Priority Data

Dec. 28, 2007 (EP) .................................... 07124133
Mar. 9, 2010 (EP) .................................... 10155926

(51) Int. Cl.
*A61B 8/14* (2006.01)
*A61B 8/08* (2006.01)
(Continued)

(52) U.S. Cl.
CPC ............ *A61B 8/5223* (2013.01); *A61B 8/481* (2013.01); *G06F 19/00* (2013.01); *G06T 7/0016* (2013.01);
(Continued)

(58) Field of Classification Search
CPC ....... A61B 8/481; A61B 8/483; A61B 8/5223; G06T 2207/10132; G06T 2207/30104; G06T 7/0016; G16H 40/63
See application file for complete search history.

(56) References Cited

U.S. PATENT DOCUMENTS

| 5,203,337 A | 4/1993 | Feldman |
| 5,287,273 A | 2/1994 | Kupfer et al. |

(Continued)

FOREIGN PATENT DOCUMENTS

| EP | 0458745 A1 | 11/1991 |
| EP | 0554213 A1 | 8/1993 |

(Continued)

OTHER PUBLICATIONS

Krix, Martin et al., "Quantification of perfusion of liver tissue and metastases using a multivessel model for replenishment kinetics of ultrasound contrast agents ," Ultrasound in Med. & Biol., vol. 30, No. 10, pp. 1355-1363, Aug. 11, 2004.

(Continued)

*Primary Examiner* — Ruth S Smith
(74) *Attorney, Agent, or Firm* — Fogg & Powers LLC

(57) ABSTRACT

An embodiment includes analyzing a body part perfused with a contrast agent, which has been pre-administered as a bolus to circulate through the body-part with at least a first passage during an analysis interval. The analyzing includes providing at least one input signal indicative of a response to an interrogation signal of a corresponding location of the body part during the analysis interval, and fitting each input signal over the analysis interval by an instance of a combined bolus function of time, based on a combination of a first simple bolus function of time modeling the first passage of the contrast agent and at least one second simple bolus (Continued)

function of time each one modeling a corresponding second passage of the contrast agent.

19 Claims, 9 Drawing Sheets

Related U.S. Application Data continuation-in-part of application No. 12/811,089, filed as application No. PCT/EP2008/068247 on Dec. 23, 2008.

(51) Int. Cl.
    *G06T 7/00*     (2017.01)
    *G16H 40/63*     (2018.01)
    *G06F 19/00*     (2018.01)

(52) U.S. Cl.
    CPC .............. *G16H 40/63* (2018.01); *A61B 8/483* (2013.01); *G06T 2207/10132* (2013.01); *G06T 2207/30104* (2013.01)

(56) References Cited

U.S. PATENT DOCUMENTS

| | | | |
|---|---|---|---|
| 5,583,902 | A | 12/1996 | Bae |
| 6,216,094 | B1 | 4/2001 | Fox Linton et al. |
| 6,445,945 | B1 | 9/2002 | Arsenault |
| 6,540,680 | B1 | 4/2003 | Kurosaki |
| 6,879,853 | B2 | 4/2005 | Meaney et al. |
| 7,069,068 | B1 | 6/2006 | Ostergaard |
| 2004/0172303 | A1 | 9/2004 | Declerck et al. |
| 2008/0139942 | A1 | 6/2008 | Gaud et al. |
| 2011/0015522 | A1 | 1/2011 | Arditi et al. |

FOREIGN PATENT DOCUMENTS

| | | |
|---|---|---|
| JP | 2000506398 | 5/2000 |
| JP | 2001178717 | 7/2001 |
| JP | 2007090075 | 4/2007 |
| JP | 2007536048 | 12/2007 |
| WO | 9115244 A2 | 10/1991 |
| WO | 9409829 A1 | 5/1994 |
| WO | 9516467 A1 | 6/1995 |
| WO | 2004110279 A1 | 12/2004 |
| WO | 05116902 A2 | 12/2005 |
| WO | 06018433 A1 | 2/2006 |
| WO | 2006067201 A2 | 6/2006 |
| WO | 06108868 A | 10/2006 |
| WO | 07054544 A1 | 5/2007 |
| WO | 2009083557 A1 | 7/2009 |
| WO | 10058014 A1 | 5/2010 |
| WO | 11110552 A1 | 9/2011 |

OTHER PUBLICATIONS

Lanza, Gregory M. et al. "Targeted Ultrasonic Contrast Agents for Molecular Imaging and Therapy", Progress in Cardiovascular Diseases, 44(1):pp. 13-31, Jul./Aug. 2001.

Linder, Jonathan R. et al., "Albumin Microbubble Persistence During Myocardial Contrast Echocardiography Is Associated With Microvascular Endothelial Glycocalyx Damage," Circulation, vol. 98 pp. 2187-2194, 1998.

Linton, R.A.F. et al., "A new method of analyzing indicator dilution curves," Cardiovascular Research, vol. 30, pp. 930-938, 1995.

Rafter, Patrick et al., "Imaging technologies and techniques," Cardiology Clinics vol. 22, pp. 181-197, 2004.

International Search Report dated May 16, 2011 for PCT/EP2011/053460, international filing date of Mar. 8, 2011 for "Initialization of Fitting Parameters for Perfusion Assessment Based on Bolus Administration" 4 pages.

International Search Report dated Apr. 20, 2009 for PCT/EP2008/068247, international filing date of Dec. 23, 2008 for "Quantification Analysis of Immobilized Contrast Agent in Medicinal Imaging Application" 3 pages.

International Preliminary Report on Patentability dated Sep. 11, 2012 for PCT/EP2011/053460, international filing date of Mar. 8, 2011 for "Initialization of Fitting Parameters for Perfusion Assessment Based on Bolus Administration" 8 pages.

International Preliminary Report on Patentability dated Jun. 29, 2010 for PCT/EP2008/068247, international filing date of Dec. 23, 2008 for "Quantification Analysis of Immobilized Contrast Agent in Medicinal Imaging Application" 7 pages.

INITIALIZATION OF FITTING PARAMETERS FOR PERFUSION ASSESSMENT BASED ON BOLUS ADMINISTRATION

CROSS REFERENCE TO RELATED APPLICATIONS

The instant application is a continuation-in-part of PCT/EP2011/053460 filed Mar. 8, 2011, which application claims priority to European Application No. 10155926.8, filed Mar. 9, 2010, which applications are herewith incorporated by reference in their entireties. The instant application is a continuation-in-part of U.S. Pat. No. 9,072,492 filed on Oct. 6, 2010 and issued Jul. 7, 2015, which patent is a national stage application of PCT/EP2008/68247 filed Dec. 23, 2008, which application claims priority to European Patent Application No. 07124133.5, filed Dec. 28, 2007, which patent and application are herewith incorporated by reference in their entireties.

TECHNICAL FIELD

A solution according to one or more embodiments relates to the diagnostic field. More specifically, a solution relates to diagnostic applications based on bolus administration of contrast agent.

BACKGROUND

Contrast agents are commonly used in diagnostic applications, such as for the assessment of blood perfusion in contrast-enhanced ultrasound imaging applications. For this purpose, during an analysis process of a specific body-part of a patient, an ultrasound contrast agent (UCA)—for example, consisting of a suspension of phospholipid-stabilized gas-filled microbubbles—is administered to the patient. The contrast agent acts as an efficient ultrasound reflector, and it can be easily detected by applying ultrasound waves and measuring echo signals that are returned in response thereto. Since the contrast agent flows at the same velocity as red-blood cells in the patient, its detection and tracking in the body-part under analysis provides information about the corresponding blood perfusion.

Particularly, in a quantitative approach, the echo signal is recorded over time during the whole analysis process for each location of the body-part, and it is fitted by a parametric function using a best-fit optimization process. This optimization process generates a time-intensity function, which consists of an instance of the parametric function being defined by the best-fit values of its fitting parameters. The values of different perfusion parameters are calculated from the time-intensity function (such as a time to peak, a mean transit time, and the like); these perfusion parameter values are then used to characterize the corresponding location (for example, for detecting and identifying a lesion). Any perfusion parameter may be calculated from the echo signal over time that is obtained in a predefined Region of Interest (ROI)—with the perfusion parameter value that is then presented as a single value. Alternatively, any perfusion parameter may be calculated from the echo signal over time of each basic portion of the body-part individually; a parametric image is then generated by graphically visualizing the perfusion parameter values of the different basic portions of the body-part (for example in a color-coded representation). The perfusion parameter values provide a quantitative assessment of the blood perfusion in the body-part (with the parametric images representing a spatial map of the perfusion parameter values throughout the body-part).

The contrast agent may be administered to the patient as a bolus (i.e., a single dose provided over a short period of time). The bolus administration is very simple, and it can be carried out by hand (for example, using a syringe); moreover, this requires a small amount of contrast agent. Different examples of quantitative analyses based on bolus administration are disclosed in WO-A-2006/108868, WO-A-2006/067201, WO-A-2009/083557, WO-A-2010/058014, and U.S. Pat. No. 6,216,094, as well as in "Quantification of perfusion of liver tissue and metastases using a multivessel model for replenishment kinetics of ultrasound contrast agents—Martin Krix, Christian Plathow, Fabian Kiessling, Felix Herth, Andreas Karcher, Marco Essig, Harry Schmitteckert, Hans-Ulrich Kauczor, And Stefan Delorme, Ultrasound in Med. & Biol., Vol. 30, No. 10, pp. 1355-1363", and "A new method of analyzing indicator dilution curves, Cardiovascular Research—R. A. F. Linton, N. W. F. Linton and D. M. Band, vol. 30, pp. 930-938, 1995 (the entire disclosures of which are herein incorporated by reference).

Particularly, WO-A-2009/083557 discloses a method for detecting and quantifying targeted contrast agent that immobilizes on a specific target. For this purpose, the echo signal is fitted by an instance of a model function based on a combination of a circulation function (modeling the circulation of the contrast agent) and a dynamic immobilization function (modeling the immobilization of the contrast agent and the decay of its echo signal). In a specific implementation, the fitting operation is performed in two optimization steps. At first, an initial portion of the echo signal is defined up to a predefined multiple of its peak instant (when the echo signal reaches the maximum value thereof). The initial portion of the echo signal is fitted by an instance of the same circulation function alone, so as to determine the values of the corresponding fitting parameters (i.e., A, m and s in the case of a lognormal distribution function). This instance of the circulation function provides a good estimate of each signal (since only a small fraction of the contrast agent immobilizes at the beginning); moreover, the dynamic immobilization function depends on the circulating function (i.e., on its integral). Therefore, the same fitting parameters A, m and s of the model function may be initialized substantially exactly to the values determined above (and constrained to vary during the corresponding optimization step within a predefined range thereof); the fitting of the echo signal by the model function may then be focused on the determination of its remaining fitting parameters alone (i.e., an immobilization parameter and a decay parameter).

Typically, the parametric function consists of a simple bolus function (for example, the lognormal distribution function), as used in classical indicator-dilution approaches, which is adapted to model the typical trend of the echo signal over time (with a wash-in followed by a wash-out of the contrast agent). However, the simple bolus function is generally unable to model a second passage of the contrast agent following a first passage thereof (for example, due to its re-circulation through the body-part, following the normal cycle of circulation of the blood in the patient). Particularly, when the second passage of the contrast agent reaches the body-part before completion of the first passage, the resulting time-intensity function is not very accurate in describing the actual trend of the echo signal over time and therefore it is unable to accurately describe the perfusion of the body-part by the contrast agent—with corresponding errors in the resulting perfusion parameter values, which adversely affect a quality of the analysis process.

In order to tackle this problem, several methods for separating the first passage from the second passage of the contrast agent have been proposed in the art—for example, as described in the above-mentioned documents U.S. Pat. No. 6,216,094 and "R. A. F. Linton, N. W. F. Linton and D. M. Band". However, these methods become unreliable when there is a substantial degree of encroachment of the second passage on the first passage and/or when the second passage starts before a peak instant of the first passage.

Alternatively, the above-mentioned document WO-A-2006/067201 proposes the use of a combined bolus function that consists of the sum of a first simple bolus function (for the first passage of the contrast agent) and a second simple bolus function (for the second passage of the contrast agent). The combined bolus function allows obtaining an accurate representation of the first passage of the contrast agent, which contains the most relevant information about the perfusion of the corresponding location of the body-part (with the perfusion parameter values being calculated from the first time-intensity function facilitating its characterization).

However, the combined bolus function now includes a high number of fitting parameters (i.e., twice the ones of the simple bolus function). Therefore, the fitting of the echo signals by the combined bolus function (for determining the corresponding time-intensity functions) is quite problematic. Particularly, this may cause instabilities in the applied algorithm (for example, because of ambiguities or convergence errors), and/or it may result in unreliable estimates of the fitting parameters (and then of the corresponding perfusion parameters); the problem is especially important when the fitting is applied on noisy echo signals.

SUMMARY

In its general terms, a solution according to one or more embodiments is based on the idea of suitably initializing the fitting parameters.

More specifically, an embodiment provides a data-processing method for analyzing a body-part perfused with a contrast agent; the contrast agent has been pre-administered as a bolus to circulate through the body-part with a first passage and possibly with at least one second passage during an analysis interval. The method includes the following steps. At least one input signal is provided; each input signal is indicative of a response to an interrogation signal (for example, ultrasound waves) of a corresponding location of the body-part (for example, a pixel, a group of pixels, or a region of interest) during the analysis interval. Each input signal is fitted over the analysis interval by an instance of a combined bolus function of time, based on a combination of a first simple bolus function of time, modeling the first passage of the contrast agent, and at least one second simple bolus function of time, each one modeling a corresponding second passage of the contrast agent (for example, the first simple bolus function and each second simple bolus function may be lognormal distribution functions); this instance of the combined bolus function is defined by the values of a set of first fitting parameters of the first simple bolus function, a set of second fitting parameters of each second simple bolus function and a delay parameter of each second simple bolus function with respect to the first simple bolus function. In an embodiment, the step of fitting each input signal includes the following steps. A peak instant of the input signal, when the corresponding response reaches an absolute peak, is estimated. A truncation interval is set within the analysis interval according to the peak instant. A truncated signal, defined by the input signal over the truncation interval, is fitted by an instance of a truncated simple bolus function of time modeling a single passage of the contrast agent during the truncation interval; this instance of the truncated simple bolus function is defined by the values of a set of truncated fitting parameters. The first fitting parameters, the second fitting parameters of each second simple bolus function and the delay parameter of each second simple bolus function are then initialized according to the values of the truncated fitting parameters.

In an embodiment, the step of fitting each input signal further includes calculating the value of a truncated mean transit time of the truncated simple bolus function, and initializing at least one fitting parameter among the first fitting parameters, the second fitting parameters of each second simple bolus function and the delay parameter of each second simple bolus function according to the value of the truncated mean transit time.

In an embodiment, the step of initializing includes initializing the delay parameter of each second simple bolus function to a fraction of the value of the truncated mean transit time.

In an embodiment, the step of initializing includes calculating the value of a first mean transit time for the first simple bolus function and the value of a second mean transit time for each second simple bolus function according to the value of the truncated mean transit time; at least one of the first fitting parameters are then initialized to the corresponding value calculated from the value of the first mean transit time, and at least one of the second fitting parameters of each second simple bolus function are then initialized to the corresponding value calculated from the value of the second mean transit time.

In an embodiment, the step of initializing includes setting the value of the first mean transit time to the value of the truncated mean transit time multiplied by a first setting factor, and setting the value of the second mean transit time for each second simple bolus function to the value of the truncated mean transit time multiplied by a second setting factor.

In an embodiment, the step of initializing includes initializing at least a further one of the second fitting parameters of each second simple bolus function to the value of the corresponding truncated fitting parameter multiplied by an initialization factor different from 1.

In an embodiment, the step of fitting each input signal further includes constraining the first fitting parameters, the second fitting parameters of each second simple bolus function and the delay parameter of each second simple bolus function according to the values of the truncated fitting parameters.

In an embodiment, the step of constraining includes constraining said at least one fitting parameter according to the value of the truncated mean transit time.

In an embodiment, the step of constraining includes constraining the delay parameter of each second simple bolus function to range between a lower delay limit and an upper delay limit, the lower delay limit and the upper delay limit being equal to the value of the truncated mean transit time multiplied by a lower delay constraining factor and an upper delay constraining factor, respectively.

In an embodiment, the step of constraining includes calculating a lower first mean transit time limit and an upper first mean transit time limit for the first simple bolus function equal to the value of the truncated mean transit time multiplied by a lower first constraining factor and an upper first constraining factor, respectively; it further includes calculating a lower second mean transit time limit and an upper second mean transit time limit for each second simple bolus function equal to the value of the truncated mean transit time multiplied by a lower second constraining factor and an upper second constraining factor, respectively. The step of constraining then includes constraining said at least one of the first fitting parameters to range between a corresponding lower first limit and a corresponding upper first limit calculated from the lower first mean transit time limit and the upper first mean transit time limit, respectively; it further includes constraining said at least one of the second fitting parameters to range between a corresponding lower second limit and a corresponding upper second limit calculated from the lower second mean transit time limit and the upper second mean transit time limit, respectively.

In an embodiment, the first simple bolus function and each second simple bolus function are lognormal distribution functions; said at least one of the first fitting parameters and said at least one of the second fitting parameters include a mean and a standard deviation of a distribution of the natural logarithm of time of the first simple bolus function and the second simple bolus function, respectively.

In an embodiment, the step of constraining includes constraining a second mean transit time of each second simple bolus function to exceed a first time to peak of the first simple bolus function.

In an embodiment, the step of constraining includes constraining at least a further one of the first fitting parameters to range between a lower further first limit and an upper further first limit equal to the value of the corresponding truncated parameter multiplied by a lower further first constraining factor and an upper further first constraining factor, respectively; it further includes constraining at least a further one of the second fitting parameters of each second simple bolus function to range between a lower further second limit and an upper further second limit equal to the value of the corresponding truncated parameter multiplied by a lower further second constraining factor and an upper further second constraining factor, respectively.

In an embodiment, the step for estimating a peak instant includes fitting the input signal over the analysis interval by an instance of an initial simple bolus function of time modeling a single passage of the contrast agent during the analysis interval, and calculating the peak instant from the initial simple bolus function.

In an embodiment, the method further includes the steps of calculating a difference signal from each input signal by subtracting the values of the corresponding combined bolus function at corresponding instants from the input signal, and fitting each difference signal by a third simple bolus function of time modeling a third passage of the contrast agent.

In an embodiment, the step of setting a truncation interval includes setting an end of the truncation interval equal to the peak instant multiplied by a truncation factor.

A further embodiment proposes a corresponding computer program; particularly, the computer program includes code means for causing a data-processing system to perform the steps of the an embodiment of the above-mentioned data-processing method when the computer program is executed on the data-processing system.

A still further embodiment proposes a corresponding computer program product. Particularly, the product includes a non-transitory computer-readable medium embodying a computer program, the computer program including code means directly loadable into a working memory of a data-processing system thereby configuring the data-processing system to perform an embodiment of the above-mentioned data-processing method.

Another embodiment provides a diagnostic system including means for performing the steps of the above-mentioned data-processing method.

A different embodiment provides a corresponding diagnostic method for analyzing a body-part. The diagnostic method includes the following steps. A contrast agent is administered to the body-part to cause the body-part to be perfused with the contrast agent; the contrast agent is administered as a bolus to circulate through the body-part with a first passage and possibly with at least one second passage during an analysis interval. An interrogation signal is applied to the body-part during the analysis interval. At least one input signal, indicative of a response to the interrogation signal of a corresponding location of the body-part during the analysis interval, is acquired; each input signal is processed according to the above-mentioned data-processing method to obtain the corresponding combined bolus function. A perfusion of each location of the body-part is then assessed according to the corresponding combined bolus function.

BRIEF DESCRIPTION OF THE DRAWINGS

One or more embodiments, as well as further features and the advantages thereof, will be best understood with reference to the following detailed description, given purely by way of a non-restrictive indication, to be read in conjunction with the accompanying drawings (wherein corresponding elements are denoted with equal or similar references and their explanation is not repeated for the sake of brevity, and the name of each entity is generally used to denote both its type and its attributes—such as its value, content and representation—for the sake of simplicity). Particularly.

DETAILED DESCRIPTION

Figure 1:
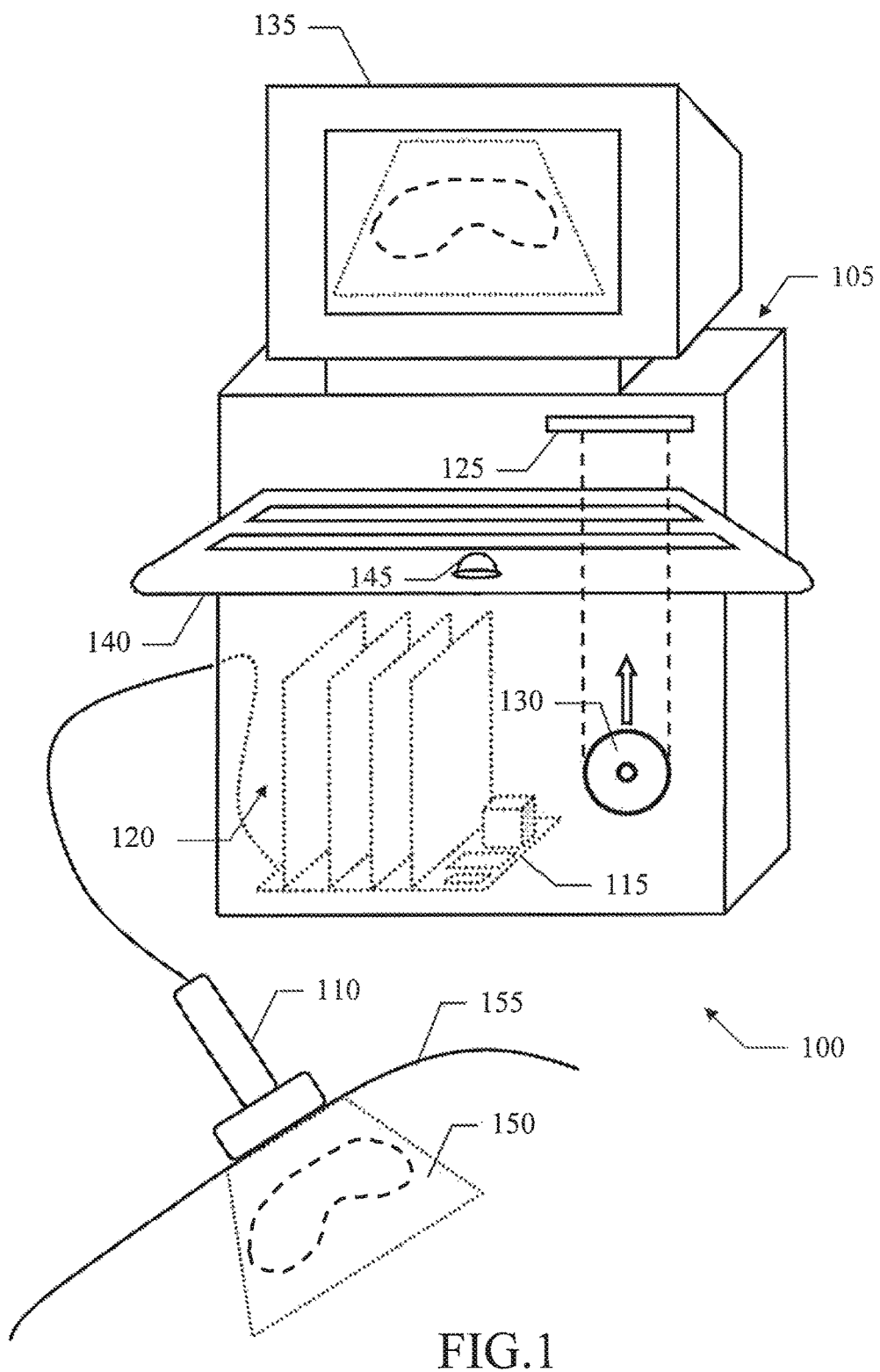
FIG. 1 shows a pictorial representation of an ultrasound scanner that can be used to practice an embodiment.

With reference in particular to FIG. 1, an ultrasound scanner 100 is illustrated that can be used to practice an embodiment. The ultrasound scanner 100 includes a central unit 105 and a hand-held transmit-receive imaging probe 110 (for example, of the array type). The imaging probe 110 transmits ultrasound waves consisting of a sequence of pulses (for example, having a center frequency between 1 and 50 MHz), and receives radio-frequency (RF) echo signals resulting from the reflection of the ultrasound pulses in a selected scanning plane; for this purpose, the imaging probe 110 is provided with a transmit/receive multiplexer, which allows using the imaging probe 110 in the above-described pulse-echo mode.

The central unit 105 houses a motherboard 115, on which the electronic circuits controlling operation of the ultrasound scanner 100 are mounted (for example, a microprocessor, a working memory and a hard-disk drive). Moreover, one or more daughter boards (denoted as a whole with the reference 120) are plugged into the motherboard 115; the daughter boards 120 provide the electronic circuits for driving the imaging probe 110 and for processing the received echo signals. The ultrasound scanner 100 can also be equipped with a drive 125 for removable disks 120 (such as CDs or DVDs). A monitor 125 displays images relating to an analysis process that is in progress. Operation of the ultrasound scanner 100 is controlled by means of a keyboard 140, which is connected to the central unit 105 in a conventional manner; for example, the keyboard 140 is provided with a trackball 145 that is used to manipulate the position of a pointer (not shown in the figure) on a screen of the monitor 125.

The ultrasound scanner 100 is used to analyze a body-part 150 of a patient 155, in order to assess a corresponding blood perfusion. For this purpose, during an analysis process of the body-part 150 a contrast agent (acting as an efficient ultrasound reflector) is administered to the patient 155. For example, the contrast agent consists of a suspension of gas bubbles in a liquid carrier; typically, the gas bubbles have diameters of the order of 0.1-5 µm, so as to allow them to pass through the capillaries of the patient 155. The gas bubbles are generally stabilized by entraining or encapsulating the gas or a precursor thereof into a variety of systems, including emulsifiers, oils, thickeners, sugars, proteins or polymers; stabilized gas bubbles are generally referred to as gas-filled microvesicles. The microvesicles include gas bubbles dispersed in an aqueous medium and bound at the gas/liquid interface by a very thin envelope involving a surfactant (i.e., an amphiphilic material), also known as microbubbles. Alternatively, the microvesicles include gas bubbles that are surrounded by a solid material envelope formed of lipids or (natural or synthetic) polymers, also known as microballoons or microcapsules. Another kind of contrast agent includes a suspension of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising gas-filled microvesicles is Sono-Vue® by Bracco International BV.

The contrast agent is administered to the patient 155 intravenously as a bolus—i.e., a single dose provided by hand with a syringe over a short period of time (of the order of 2-20 seconds). The contrast agent circulates within a vascular system of the patient 155, so as to perfuse the body-part 150. At the same time, the imaging probe 110 is placed in contact with the skin of the patient 155 in the area of the body-part 150. A series of ultrasound pulses with low acoustic energy (such as with a mechanical index MI=0.01-0.1) is applied to the body-part 150, so as to induce a negligible destruction of the contrast agent (such as less than 5%, and, for example, less than 1% of its local concentration between successive ultrasound pulses). The echo signals that are recorded in response to the ultrasound pulses—at successive acquisition instants over time during an analysis interval (for example, at a rate of about 10-20 acquisitions per second during 1-3 minutes)—provide a representation of basic portions of the body-part 150 (in a slice thereof corresponding to the selected scanning plane) during the analysis process. The echo signals result from the superimposition of different contributions generated by the contrast agent (if present) and the surrounding tissue. For example, the ultrasound scanner 100 operates in a contrast-specific imaging mode so as to substantially remove, or at least reduce, the dominant (linear) contribution of tissue in the echo signals, with respect to the (non-linear) contribution of the contrast agent; examples of contrast-specific imaging modes include harmonic imaging (HI), pulse inversion (PI), power modulation (PM) and contrast pulse sequencing (CPS) techniques, as described, for example, in "Rafter et al., Imaging technologies and techniques, Cardiology Clinics 22 (2004), pp. 181-197" (the entire disclosure of which is herewith incorporated by reference).

The echo signal of each location of the body-part 150 (consisting of one or more basic portions thereof) is then fitted by an instance of a (model) parametric function of time, referred to as time-intensity function; particularly, the time-intensity function is defined by the values of a set of fitting parameters of the parametric function; these fitting parameter values are chosen as those that make the resulting time-intensity function best follow a trend of the echo signal over time. The time-intensity functions so obtained can then be used to calculate the values of different perfusion parameters of the corresponding locations of the body-part 150 (providing useful information for their characterization); examples of these perfusion parameters are a Time to Peak, or TP (representing a time required to reach a maximum of the echo signal), a mean Transit Time, or mTT (representing a time required by the contrast agent to perfuse the body-part), and an Area Under the Curve, or AUC (representing a relative regional tissue blood volume).

Figure 2A:
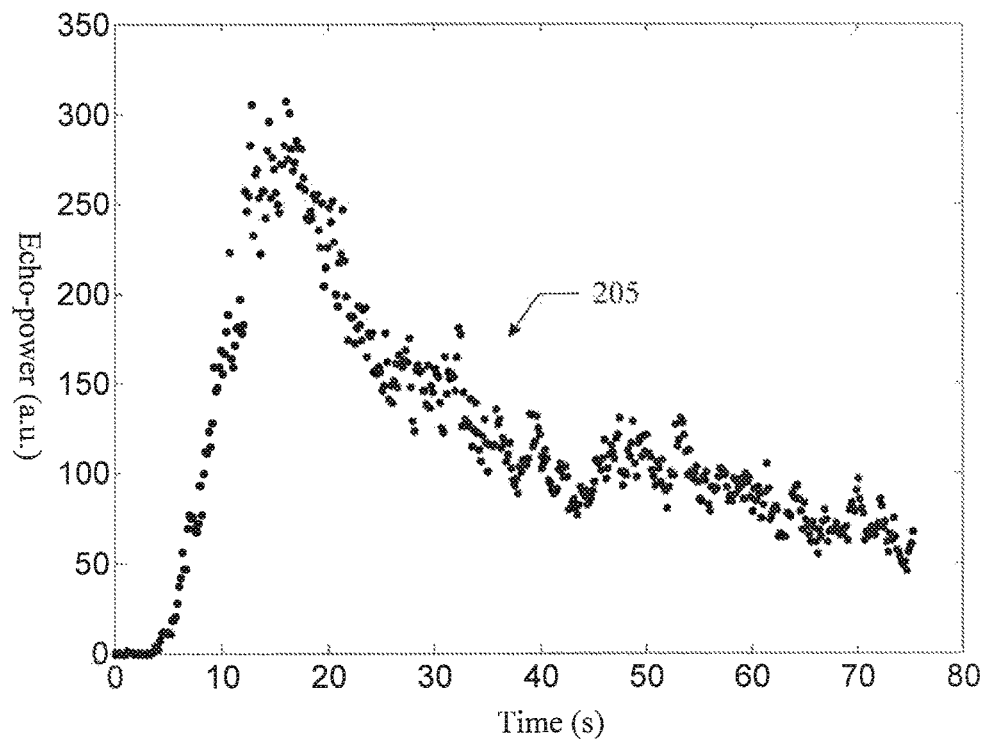
FIG. 2A shows an example of an echo signal representing the echo power recorded over time for a generic location of a body-part during an analysis process thereof according to an embodiment.

An example of an echo signal representing the echo power recorded over time for a generic location of a body-part during the analysis process is shown in FIG. 2A. Particularly, the figure includes a diagram with a sequence of signal dots 205, which represent the echo power—on the ordinate axis in terms of arbitrary units (a.u.)—recorded at the time of the corresponding acquisition instants—on the abscissa axis in seconds from the time of administration of the contrast agent. The echo signal 205 was obtained in vivo by imaging a prostate after a bolus injection of 2.4 mL of SonoVue.

The contrast agent administered to the patient circulates within his/her vascular system so as to perfuse the body-part under analysis. Particularly, during a first (main) passage of the contrast agent through the body-part following its administration (from about 0 s to 15 s in the example at issue), the echo power increases as a result of a wash-in of the contrast agent that reaches the body-part; once the echo power has reached its peak (at about 15 s in the example at issue), it starts decreasing as a result of a wash-out of the contrast agent that leaves the body-part (from about 15 s to 75 s in the example at issue).

In the meanwhile, the contrast agent continues to circulate through the vascular system of the patient during the wash-out phase in the body part, being gradually diluted in the blood so that a new inflow of the contrast agent in the body-part decreases at every next (secondary) passage thereof—substantially disappearing, for example, after a second passage. Therefore, during the wash-out phase the echo signal 205 exhibits a transient increase (lower than the above-mentioned peak) as a result of the second passage of the contrast agent (from about 20 s to 75 s in the example at issue).

Figure 2B:
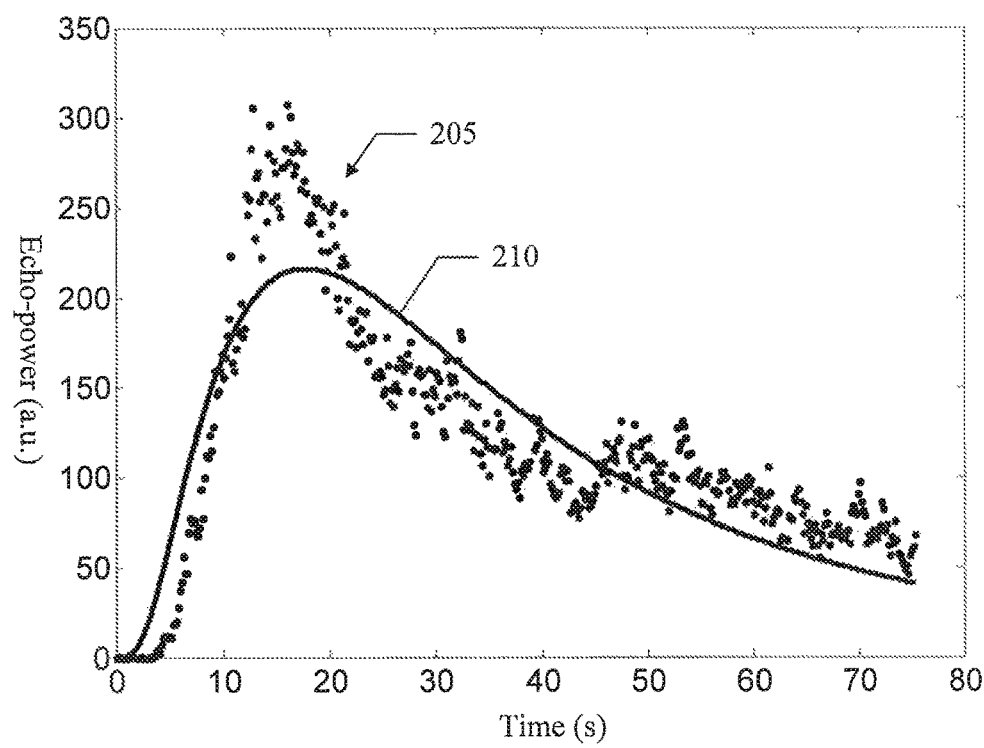
FIG. 2B shows an example of a time-intensity function based on a simple bolus function that fits this echo signal according to an embodiment.

An example of a time-intensity function (based on a simple bolus function) that fits the echo signal 205 of FIG. 2A is shown in FIG. 2B. This time-intensity function is represented with a curve 210, which plots the echo power (on the ordinate axis) as a function of time (on the abscissa axis).

Particularly, the time-intensity function 210 is an instance of a simple bolus function that consists of the lognormal distribution function (wherein the natural logarithm of its independent variable follows a normal distribution function):

$$B_s(t) = O_s + A_s \cdot \frac{e^{-\frac{[ln(t)-m_s]^2}{2s_s^2}}}{t \cdot s_s \cdot \sqrt{2\pi}},$$

where t is the independent variable representing the time (measured from the time of administration of the contrast agent) and $B_s(t)$ is the dependent variable representing the echo power (at the time t); the simple bolus function $B_s(t)$ includes a fitting parameter $O_s$ (an offset), a fitting parameter $A_s$ (an amplitude factor representing the perfusion parameter AUC), a fitting parameter $m_s$ (the mean of the corresponding distribution of the natural logarithm of the variable t), and a fitting parameter $s_s$ (the standard deviation of the corresponding distribution of the natural logarithm of the variable t). The specific instance of the simple bolus function $B_s(t)$ defining the time-intensity function 210 is then determined by the actual values of its fitting parameters $O_s$, $A_s$, $m_s$ and $s_s$.

As can be seen, the time-intensity function 210 roughly follows the typical trend of the echo signal 205 over time (with its wash-in phase, peak, and wash-out phase). However, the resulting fitting is not very accurate, so that the time-intensity function 210 may provide erroneous values of the resulting perfusion parameters. For example, the values of the perfusion parameters AUC and mTT being calculated from the time-intensity function 210 are:

$$AUC = A_s = 10,347, \text{ and}$$

$$mTT = e^{m_s + \frac{s_s^2}{2}} = 45.14 \text{ s}.$$

The values of the same perfusion parameters AUC and mTT being calculated directly (i.e., numerically) from a portion of the echo signal 205 including its peak (for example, from 0 s to 25 s) are instead:

AUC=3,693, and mTT=16.26 s.

Therefore, the values of the perfusion parameters AUC and mTT derived from the time-intensity function 210 are largely overestimated (as compared to their actual values calculated from the echo signal 205).

The discrepancy between the values of the perfusion parameters derived from the time-intensity function 210 and calculated from the echo signal 205 is mainly due to limitations of the simple bolus function $B_s(t)$ in modeling the second passage of the contrast agent through the body-part; indeed, the simple bolus function $B_s(t)$ only describes bolus kinetics of substantially perfect mixing chambers, as used in indicator dilution theory (without any re-circulation). Particularly, the simple bolus function $B_s(t)$ is characterized by a single exponential decay rate during the wash-out phase; conversely, the second passage of the contrast agent causes a change in the exponential decay rate of the echo signal 205 during the wash-out phase, which cannot be modeled by the simple bolus function $B_s(t)$.

Figure 2C:
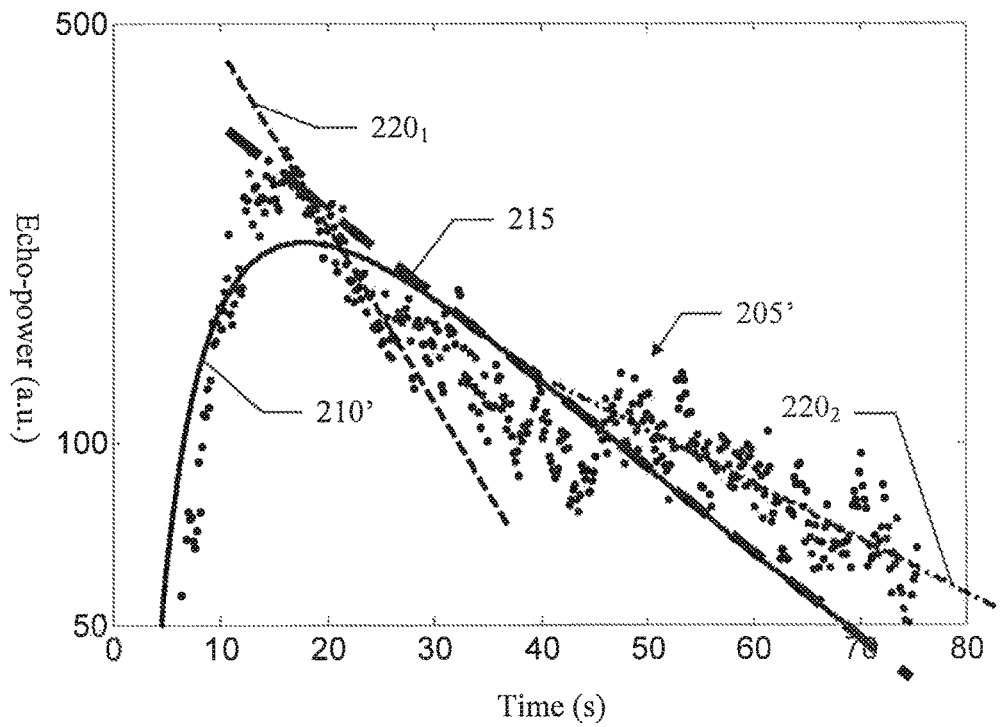
FIG. 2C shows the echo signal and the time-intensity function of FIG. 2B plotted on a semi-logarithmic scale according to an embodiment.

This is better explained in FIG. 2C, which shows the echo signal and the time-intensity function of FIG. 2B plotted on a semi-logarithmic scale (on the ordinate axis for the echo power). In this case, the echo signal and the time-intensity function are represented with a sequence of signal dots 205' and a time-intensity curve 210', respectively (which provide the logarithm of the echo power as a function of time).

Therefore, on a logarithmic scale, the exponential decay rates of the echo signal 205' and of the time-intensity function 210' are now represented by their slopes. As can been seen, the time-intensity function 210' has a constant exponential decay rate, as indicated by a straight line 215 being tangent to its curve (in thick dashed line). On the contrary, the echo signal 205' has two different exponential decay rates. Particularly, at the beginning of the wash-out phase, the echo signal 205' has a higher exponential decay rate, due to the wash-out of the first (main) passage of the contrast agent, as indicated by a straight line 220₁ (in thin dashed line); at a later instant, the echo signal 205' has a lower exponential decay rate, due to the wash-out of the second passage of the contrast agent, as indicated by a straight line 220₂ (in thin dashed line).

Figure 2D:
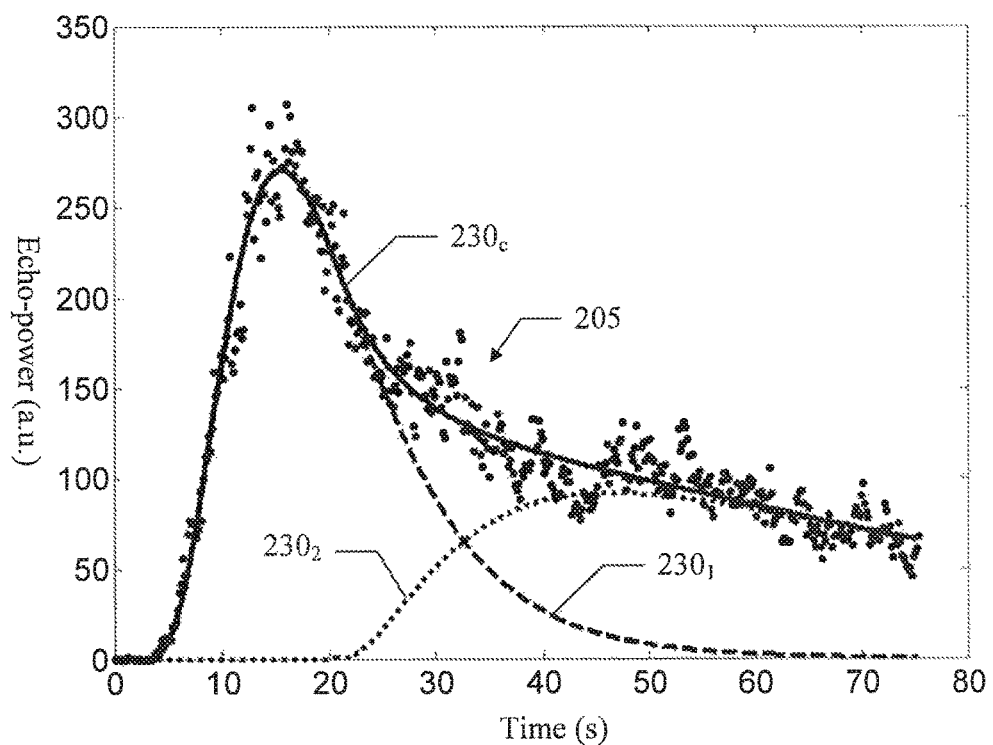
FIG. 2D shows an example of a time-intensity function based on a combined bolus function that fits the same echo signal according to an embodiment.

An example of a time-intensity function (based on a combined bolus function) that fits the same echo signal 205 of FIG. 2A is instead shown in FIG. 2D. This time-intensity function is represented with a curve 230$_c$ (again plotting the echo power as a function of time).

Particularly, the time-intensity function 230$_c$ is an instance of a combined bolus function that consists of the sum of a first (simple) bolus function for the first passage of the contrast agent and a second (simple) bolus function for the second passage of the contrast agent:

$$B_c(t) = O_c + A_1 \cdot \frac{e^{-\frac{[ln(t)-m_1]^2}{2s_1^2}}}{t \cdot s_1 \cdot \sqrt{2\pi}} + A_2 \cdot \frac{e^{-\frac{[ln(t-\Delta t)-m_2]^2}{2s_2^2}}}{t \cdot s_2 \cdot \sqrt{2\pi}};$$

the combined bolus function $B_c(t)$ now includes a fitting parameter $O_c$ (a common offset), a fitting parameter $\Delta t$ (representing a time delay of the second passage with respect to the first passage), the fitting parameters $A_1$, $m_1$, $s_1$ as above referring to the first passage of the contrast agent, and the fitting parameters $A_2$, $m_2$, $s_2$ as above referring to the second passage of the contrast agent. The specific instance of the combined bolus function $B_c(t)$ defining the time-intensity function 230$_c$ is then determined by the actual values of its fitting parameters $O_c$, $A_1$, $m_1$, $s_1$, $A_2$, $m_2$, $s_2$ and $\Delta t$.

In addition, it is also possible to determine (from the time-intensity function $230_c$) the instance of the first bolus function $B_1(t)$ (referred to as first time-intensity function) and the instance of the second bolus function $B_2(t)$ (referred to as second time-intensity function), which are represented in the same diagram with a curve $230_1$ and a curve $230_2$, respectively. Therefore, the first time-intensity function $230_1$ represents the evolution over time of the echo power during the first passage of the contrast agent, whereas the second time-intensity function $230_2$ represents the evolution over time of the echo power during the second passage of the contrast agent. As a result, it is possible to separate the first passage of the contrast agent (containing the most relevant information about the perfusion of the corresponding location of the body-part) from its second passage.

In this case, the time-intensity function $230_c$ precisely follows the trend of the echo signal 205 (with its wash-in phase, peak, and wash-out phase). Moreover, the resulting fitting is very accurate, so that the time-intensity function $230_c$ provides correct values of the resulting perfusion parameters. For example, the values of the perfusion parameters AUC and mTT being derived from the first time-intensity function $230_1$:

$$AUC = A_1 = 5,071, \text{ and}$$

$$mTT = e^{m_1 + \frac{s_1^2}{2}} = 20.71 \text{ s}$$

are very similar to their actual values calculated from the echo signal 205—i.e., 3,693 and 16.26 s, respectively.

Figure 2E:
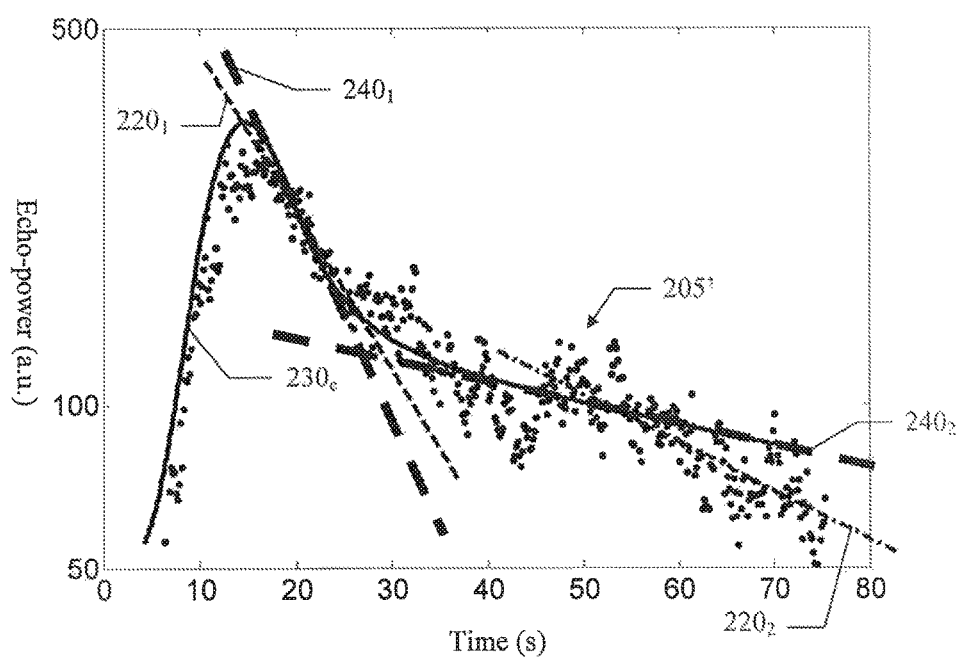
FIG. 2E shows the echo signal and the time-intensity function of FIG. 2D plotted on a semi-logarithmic scale according to an embodiment, FIG. 3A

Indeed, the combined bolus function $B_c(t)$ is now capable of accurately modeling the first and second passages of the contrast agent through the body-part thanks to its double exponential decay rate during the wash-out phase. This is better explained in FIG. 2E, which shows the echo signal and the time-intensity function of FIG. 2D plotted on a semi-logarithmic scale. In this case, the echo signal is represented with the same sequence of signal dots 205' as above, while the time-intensity function is represented with a curve $230_c$' (again displaying the logarithm of the echo power as a function of time). As can been seen, the time-intensity function $230_c$' now has two different exponential decay rates (like the echo signal 205'). Particularly, at the beginning of the wash-out phase the time-intensity function $230_c$' has a higher exponential decay rate, as indicated by a straight line $240_1$ being tangent to its curve (in thick dashed line); at a later instant, the time-intensity function $230_c$' has a lower exponential decay rate, as indicated by a straight line $240_2$ being tangent to its curve (in thick dashed line). These exponential decay rates $240_1$ and $240_2$ then correspond to the different exponential decay rates $220_1$ and $220_2$ (in thin dashed line) of the echo signal 205'—being due to the wash-out during the first passage and the second passage of the contrast agent, respectively.

However, the combined bolus function $B_c(t)$ includes a high number of fitting parameters $O_c$, $A_1$, $m_1$, $s_1$, $A_2$, $m_2$, $s_2$ and $\Delta t$; therefore, the fitting of each echo signal by the combined bolus function $B_c(t)$ for determining the corresponding time-intensity function requires the optimization of at least seven fitting parameters—disregarding the fitting parameter $O_c$ that may be assessed separately.

For this purpose, in an embodiment, a dedicated procedure for initializing the fitting parameters $A_1$, $m_1$, $s_1$, $A_2$, $m_2$, $s_2$ and $\Delta t$ is provided. Particularly, an exemplary implementation of this solution is shown in FIG. 3A-FIG. 3B.

Figure 3A:
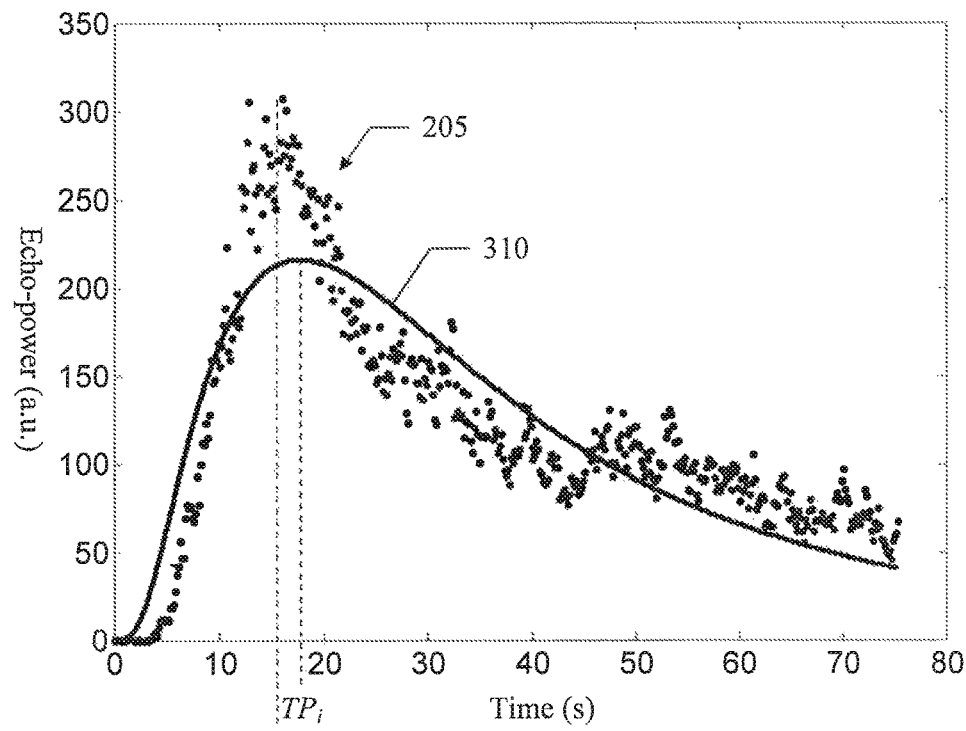
-FIG. 3B shows an exemplary implementation of the solution according to an embodiment of the invention according to an embodiment.

Starting from FIG. 3A, the echo signal 205 is at first fitted by an instance of the simple bolus function $B_s(t)$—referred to as initial time-intensity function (defined by corresponding values of its fitting parameters, referred to as initial fitting parameter values $O_i$, $A_i$, $m_i$ and $s_i$); the initial time-intensity function is represented in the same diagram of FIG. 2A with a curve 310. The initial time-intensity function 310 is then used to calculate the value of its time to peak TP (referred to as initial time-to-peak value $TP_i$).

As pointed out above, the accuracy of the initial time-intensity function 310 is not very high, so that the initial time-to-peak value $TP_i$ only provides a rough estimate of its actual peak instant $TP_i'$ in the echo signal 205 (for example, $TP_i$=17.5 s against $TP_i'$=15 s in the example at issue). However, this is not a problem, since the above-described operation is only aimed at identifying a portion of the echo signal 205 for the initialization of the fitting parameters of the combined bolus function $B_c(t)$ (for which no particular precision is required).

Figure 3B:
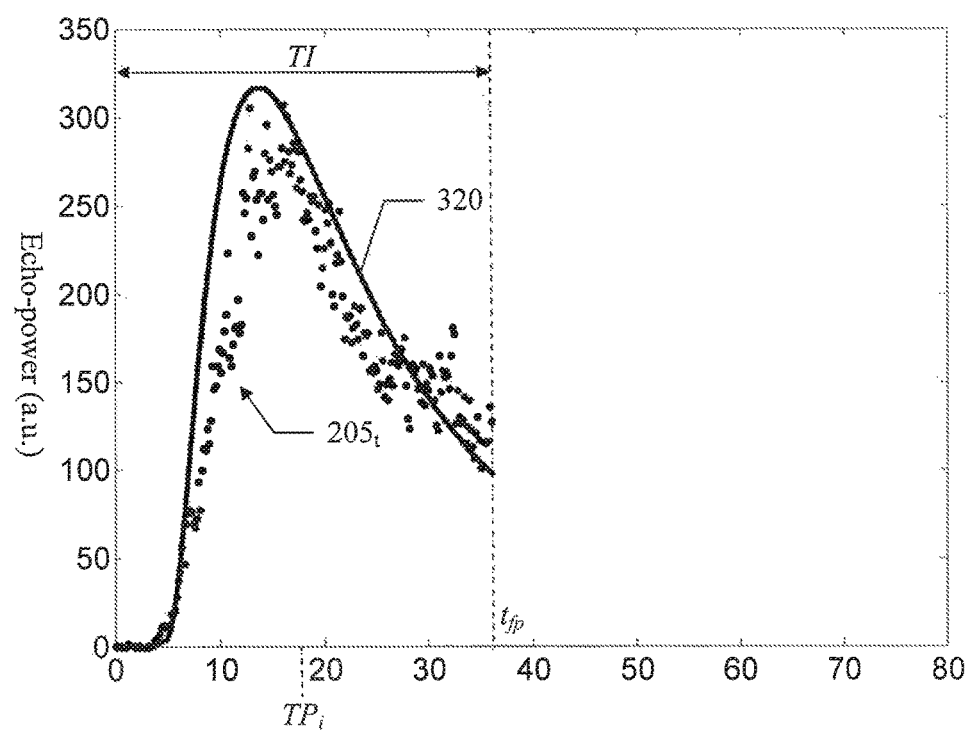

Moving to FIG. 3B, a first passage time $t_{fp}$ is calculated from the initial time-to-peak value $TP_i$ (for example, equal to twice the time-to-peak value $TP_i$—i.e., $t_{fp}$=2·17.5=35 s in the example at issue). The first passage time $t_{fp}$ defines a truncation interval TI (from the time of administration of the contrast agent to the first passage time $t_{fp}$). A truncated echo signal (represented with a corresponding sequence of signal dots $205_t$ is then obtained by discarding the echo signal outside the truncation interval TI. Therefore, to a first approximation, the truncated echo signal $205_t$ may be deemed representative of the first passage of the contrast agent only (since in this phase the contribution of the second passage of the contrast agent is limited).

The truncated echo signal $205_t$ is now fitted by another instance of the same simple bolus function $B_s(t)$—referred to as truncated time-intensity function (again defined by corresponding values of its fitting parameters—referred to as truncated fitting parameter values $O_t$, $A_t$, $m_t$ and $s_t$); the truncated time-intensity function is represented in the same diagram with a curve 320. Therefore, the truncated time-intensity function 320 now follows the trend of the truncated echo signal $205_t$ over time with a higher accuracy (because of the reduced contribution of the second passage of the contrast agent in the truncated interval TI). The truncated fitting parameter values $A_t$, $m_t$ and $s_t$ are then used to initialize the fitting parameters $A_1$, $m_1$, $s_1$, $A_2$, $m_2$, $s_2$ and $\Delta t$ of the combined bolus function $B_c(t)$ for fitting the original (complete) echo signal (for example, by setting them to a predefined multiple thereof).

The above-described embodiment strongly facilitates the fitting operations (of the echo signals by the combined bolus function $B_c(t)$). As a result, it is possible to avoid (or at least substantially reduce) any risk of instabilities in the applied algorithm. In any case, this increases the accuracy of the time-intensity functions (in precisely describing the perfusion of the body-part by the contrast agent), providing a more robust estimate of the perfusion parameters that are calculated from the time-intensity functions. All of the above has a beneficial effect on the quality of the analysis process. These advantages are particularly evident when the fitting is applied on noisy echo signals.

Figure 4A:
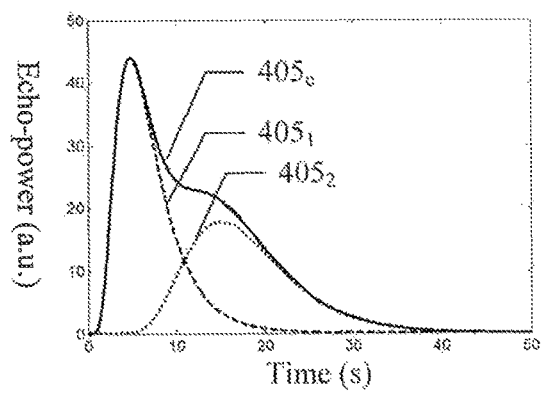
FIG. 4A-FIG. 4C, FIG. 5A-FIG. 5C, and FIG. 6A-FIG. 6C show different examples of application of an embodiment.
Figure 4B:
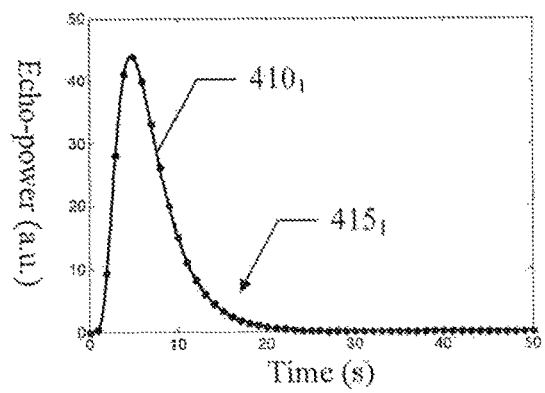
Figure 4C:
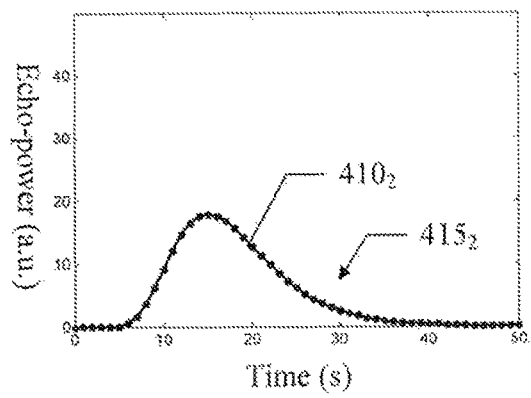

An example of application of an embodiment is shown in FIG. 4A-FIG. 4C.

Particularly, starting from FIG. 4A, a first test function was generated to simulate a first passage of the contrast agent through the body-part; the first test function is represented in the figure with a corresponding curve $405_1$ (plotted as a dashed line); likewise, a second test function was generated to simulate a second passage of the contrast agent; the second time-intensity function is represented in the figure with a corresponding curve $405_2$ (plotted as a dotted line). A combined test function was calculated by summing the first test function and the second test function; the combined test function is represented in the figure with a corresponding curve $405_c$ (plotted as a solid line). A test data array was then obtained by evaluating the combined test function $405_c$ over time. In this case, the second test function $405_2$ has a substantial degree of encroachment on the first test function $405_1$, resulting in a highly distorted combined test function $405_c$.

The fitting of this test data array with the application of the above-described solution provided a first time-intensity function that is represented in FIG. 4B with a corresponding curve $410_1$. A first test data array (obtained by evaluating the first test function over time) is represented in the figure with a corresponding sequence of test dots $415_1$. As can be seen, the first time-intensity function $410_1$ superimposes substantially perfectly on the first test data array $415_1$.

Likewise, the same fitting provided a second time-intensity function that is represented in FIG. 4C with a corresponding curve $410_2$. A second test data array (obtained by evaluating the second test function over time) is represented in the figure with a corresponding sequence of test dots $415_2$. As can be seen, the second time-intensity function $410_2$ superimposes substantially perfectly on the second test data array $415_2$.

Therefore, an embodiment is able to represent the first and second passages substantially perfectly, even when there is a substantial degree of encroachment of the second passage on the first passage. This is confirmed by the values of the fitting parameters of the first and second time-intensity functions (i.e., mTT=7, s=0.5 and AUC=300 for the first time-intensity function, and mTT=18, s=0.35 and AUC=250 for the second time-intensity function), which are substantially exactly the same as the values of the corresponding fitting parameters used for generating the first and second test functions.

Figure 5A:
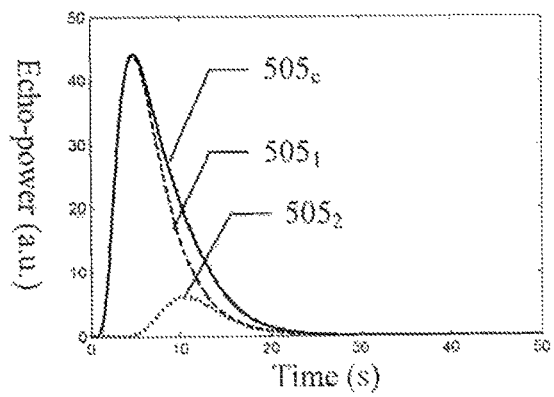
Figure 5B:
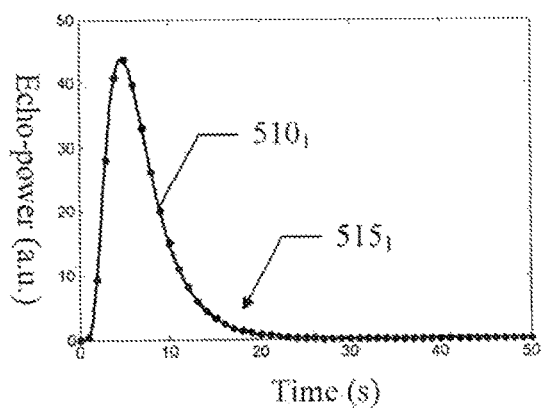
Figure 5C:
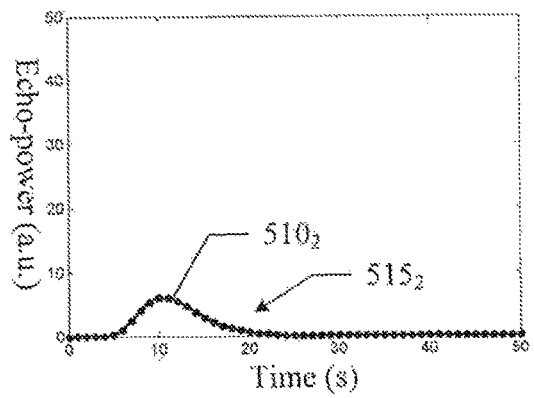

A further example of application of an embodiment is shown in FIG. 5A-FIG. 5C.

Particularly, starting from FIG. 5A a first test function (represented in the figure with a corresponding curve $505_1$ plotted as a dashed line) and a second test function (represented in the figure with a corresponding curve $505_2$ plotted as a dotted line) were generated as above to simulate a first passage and a second passage of the contrast agent through the body-part, respectively; a combined test function (represented in the figure with a corresponding curve $505_c$ plotted as a solid line) was calculated by summing the first test function and the second test function, and a test data array was then obtained by evaluating the combined test function $505_c$ over time. In this case, the second test function $505_2$ is totally encroached with the first test function $505_1$ (since the second test function $505_2$ starts before the peak instant of the first test function $505_1$), resulting in a minimal distortion of the combined test function $505_c$.

The fitting of this sequence of test data with the application of the above-described solution provided a first time-intensity function that is represented in FIG. 5B with a corresponding curve $510_1$. A first test data array (obtained by evaluating the first test function over time) is represented in the figure with a corresponding sequence of test dots $515_1$. As can be seen, the first time-intensity function $510_1$ superimposes substantially perfectly on the first test data array $515_1$.

Likewise, the same fitting provided a second time-intensity function that is represented in FIG. 5C with a corresponding curve $510_2$. A second test data array (obtained by evaluating the second test function over time) is represented in the figure with a corresponding sequence of test dots $515_2$. As can be seen, the second time-intensity function $510_2$ superimposes substantially perfectly on the second test data array $515_2$.

Therefore, an embodiment is able to represent the first and second passages substantially perfectly, even when there is a total encroachment of the second passage on the first passage. This is confirmed by the values of the fitting parameters of the first and second time-intensity functions (i.e., mTT=7, s=0.5 and AUC=300 for the first time-intensity function, and mTT=12, s=0.3 and AUC=50 for the second time-intensity function), which are substantially exactly the same as the values of the corresponding fitting parameters used for generating the first and second test functions.

Figure 6A:
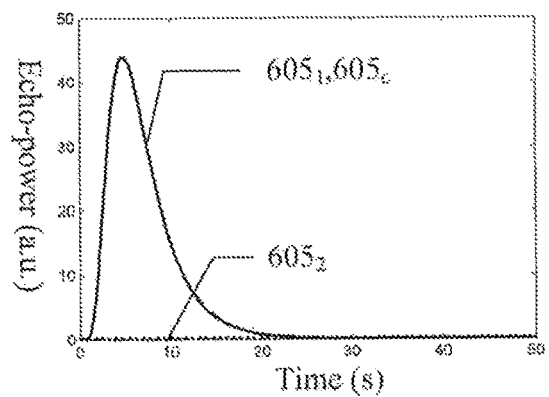
Figure 6B:
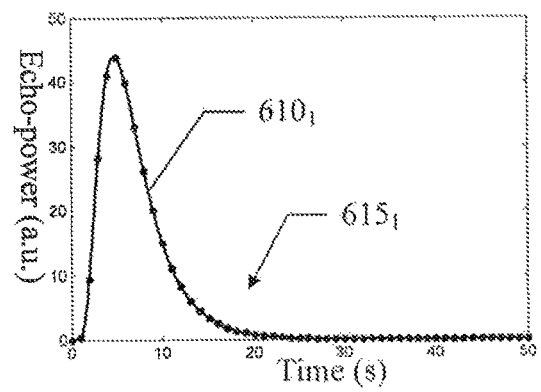
Figure 6C:
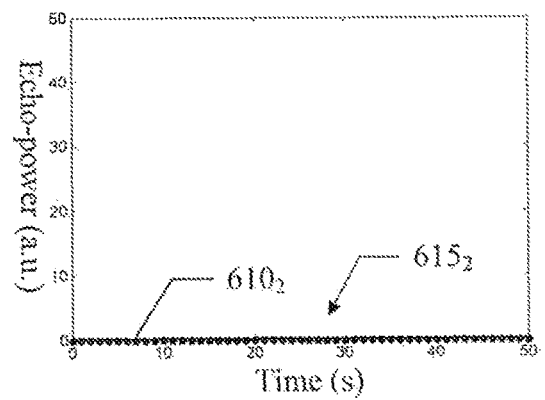

A different example of application of an embodiment is shown in FIG. 6A-FIG. 6C.

Particularly, starting from FIG. 6A a first test function (represented in the figure with a corresponding curve $605_1$ plotted as a dashed line) and a second test function (represented in the figure with a corresponding curve $605_2$ plotted as a dotted line) were generated as above to simulate a first passage and a second passage of the contrast agent through the body-part, respectively; a combined test function (represented in the figure with a corresponding curve $605_c$ plotted as a solid line) was calculated by summing the first test function and the second test function, and a test data array was then obtained by evaluating the combined test function $605_c$ over time. In this case, the second test function $605_2$ always remains zero (i.e., no re-circulation is present), with the combined test function $605_c$ that is completely determined by the first test function $605_1$.

The fitting of this sequence of test data with the application of the above-described solution provided a first time-intensity function that is represented in FIG. 6B with a corresponding curve $610_1$. A first test data array (obtained by evaluating the first test function over time) is represented in the figure with a corresponding sequence of test dots $615_1$. As can be seen, the first time-intensity function $610_1$ superimposes substantially perfectly on the first test data array $615_1$.

Likewise, the same fitting provided a second time-intensity function that is represented in FIG. 6C with a corresponding curve $610_2$. A second test data array (obtained by evaluating the second test function over time) is represented in the figure with a corresponding sequence of test dots $615_2$. As can be seen, the second time-intensity function $610_2$ superimposes substantially perfectly on the second test data array $615_2$.

Therefore, an embodiment is able to represent the first and second passages substantially perfectly, even in the extreme situation when the second passage of the contrast agent is absent. This is confirmed by the values of the fitting parameters of the first and second time-intensity functions (i.e., mTT=7, s=0.5 and AUC=300 for the first time-intensity function, and AUC<0.001 for the second time-intensity function), which are substantially the same as the values of the corresponding fitting parameters used for generating the first and second test functions (i.e., mTT=7, s=0.5 and AUC=300 for the first test function, and AUC=0 for the second test function).

Figure 7:
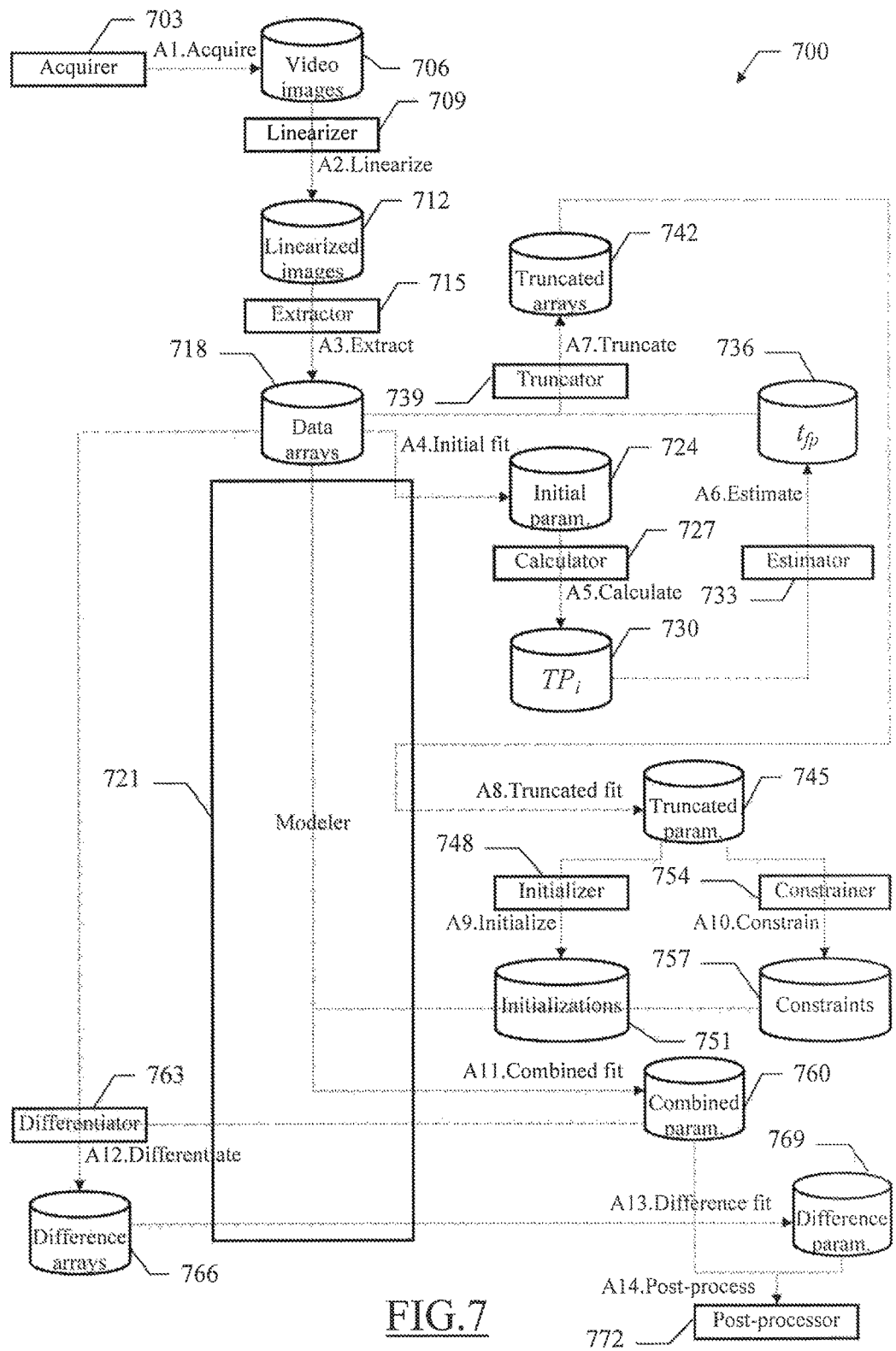
FIG. 7 shows a collaboration diagram representing the roles of the main components that may be used to implement an embodiment.

A collaboration diagram representing the roles of the main software and/or hardware components that may be used to implement an embodiment is illustrated in FIG. 7. These components are denoted as a whole with the reference 700; particularly, the information (programs and data) is typically stored on the hard-disk and loaded (at least partially) into the working memory of the ultrasound scanner when the programs are running, together with an operating system and other application programs (not shown in the figure). The programs are initially installed onto the hard disk, for example, from DVD-ROM. More specifically, the figure describes the static structure of the system (by means of the corresponding components) and its dynamic behavior (by means of a series of exchanged messages, each one representing a corresponding action, denoted with sequence numbers preceded by the symbol "A").

Particularly, an acquirer 703 includes a driver that controls the imaging probe. For example, this driver is provided with a transmit beam former and pulsers for generating the ultrasound pulses to be applied to the body-part under analysis; the imaging probe then receives the analog RF echo signals that are reflected by the different basic portions of the body-part in its slice at the selected scanning plane. These analog RF echo signals are supplied to a receive processor, which pre-amplifies the analog RF echo signals and applies a preliminary time-gain compensation (TGC); the analog RF echo signals are then converted into digital values by an Analog-to-Digital Converter (ADC), and combined into focused beam signals through a receive beam former. The digital echo signals so obtained are, for example, processed through further digital algorithms and other linear or non-linear signal conditioners (for example, a post-beam-forming TGC). Particularly, the receive processor applies a contrast-specific algorithm to suppress the contribution of the tissue (such as based on the above-mentioned HI, PI, PM or CPS techniques). The digital echo signals are then demodulated, log-compressed (in order to obtain images with well-balanced contrast), and scan-converted into a video format. This process generates a sequence of contrast-specific video images, each one representing the selected slice of the body-part at the corresponding acquisition instant. Each video image is defined by a matrix of cells (for example, with 512 rows×512 columns) for pixels representing the different basic portions of the body-part. Each cell of the video image stores a pixel value (for example, coded on 8 bits) that defines a brightness of the corresponding video pixel; for example, in grayscale video images the pixel value increases from 0 (black) to 255 (white) as a function of the echo signal intensity of the corresponding basic portion of the body-part.

At the beginning of the analysis process, an operator of the ultrasound scanner actuates the imaging probe and moves it around the body-part to be analyzed (before administering any contrast agent). The corresponding video images are displayed in real-time as soon as they are acquired; the operator then chooses a slice of the body-part to be analyzed (for example, including a suspicious lesion) and keeps the imaging probe in a fixed position. The contrast agent is now administered to the patient, and the ultrasound scanner acquires a sequence of video images that represents this slice of the body-part over time; the sequence of video images so obtained is saved into a repository 706 for off-line analysis (action "A1.Acquire").

The video images 706 are supplied to a linearizer 709, which processes each pixel value thereof so as to make it directly proportional to the corresponding local concentration of the contrast agent. For example, this result can be achieved by applying an inverse log-compression (to reverse the effect of its application by the acquirer 703), and then squaring the values so obtained (as described in WO-A-2004/110279, the entire disclosure of which is herein incorporated by reference). Typically, this operation is limited to a portion of the video images 706, corresponding to a region of interest of the body-part that has been selected by the operator (for example, by drawing a line around it on one of the video images 706 with the help of the trackball). As a result, the linearizer 709 generates a corresponding sequence of linearized images, which is saved into a repository 712 (action "A2.Linearize").

An extractor 715 accesses the repository 712 of the linearized images for extracting one or more data arrays each one for a corresponding location of the body-part. Particularly, when the analysis process is performed at the level of pixels, a data array is created for each pixel of the linearized images 712; the data array includes a sequence of the corresponding pixel values along the linearized images 712. Conversely, when the analysis process is performed at the level of groups of pixels, in each linearized image 712 a single group value is calculated for each group of pixels (for example, by averaging the corresponding pixel values); a data array is then created for each group of pixels by including a sequence of the corresponding group values along the linearized images 712. Moreover, the analysis process may also be performed at the level of the whole region of interest, wherein a single data array is created from the corresponding pixel values as described above. In any case, the data arrays are then stored into a repository 718 (action "A3.Extract").

The data arrays 718 are supplied to a modeler 721. The modeler 721 at first fits each data array 718 by an instance of the simple bolus function $B_s(t)$, so as to obtain the corresponding initial time-intensity function (being defined by the initial fitting parameter values $O_i$, $A_i$, $m_i$ and $s_i$). This result is achieved by applying well known error-minimization algorithms; for example, when the fitting operation is based on the gradient descent algorithm, at each iteration of an optimization loop a direction is determined along which a difference between a current instance of the simple bolus function $B_s(t)$ and the data array 718 decreases most rapidly (i.e., the corresponding gradient is the lowest); the fitting parameters of the simple bolus function $B_s(t)$ are then updated in this direction for a next iteration of the optimization loop (until the difference is smaller than a predefined threshold value). The sets of initial fitting parameter values $O_i$, $A_i$, $m_i$ and $s_i$ for the different locations (i.e., pixels, groups of pixel, or region of interest) are stored into a repository 724 (action "A4.Initial fit").

The sets of initial fitting parameter values $O_i$, $A_i$, $m_i$ and $s_i$ are supplied from the repository 724 to a calculator 727. For each location, the calculator 727 calculates the initial time-to-peak value $TP_i$ of the corresponding initial time-intensity function:

$$TP_i = e^{m_i - s_i^2}.$$

The time-to-peak values $TP_i$ for the different locations are stored into a repository 730 (action "A5.Calculate"). This feature is particularly advantageous, since it allows calculating the peak instant of the echo signal in each location analytically.

The time-to-peak values $TP_i$ are then supplied from the repository 730 to an estimator 733. For each location, the estimator 733 calculates the corresponding first passage time $t_{fp}$. Particularly, the first passage time $t_{fp}$ is set to:

$$t_{fp} = \beta \cdot TP_i,$$

wherein β is a factor, for example, comprised between 1 and 3, and such as between 1.5 and 2.5 (such as β=2). The first passage times $t_{fp}$ for the different locations are stored into a repository 736 (action "A6.Estimate").

A truncator 739 accesses both the repository 718 of the data arrays and the repository 736 of the first passage times $t_{fp}$. For each location, the truncator 739 truncates the corresponding data array 718 by discarding the values thereof outside the truncation interval TI, which is defined from the time origin (corresponding to the time of administration of the contrast agent) to the first passage time $t_{fp}$. For this purpose, a first passage number $N_{fp}$ is calculated as the integer of the ratio between the first passage time $t_{fp}$ and an acquisition period of the video images 706; the data array 718 is then truncated by limiting it to the values thereof up to the first passage number $N_{fp}$. An indication of the truncated (data) arrays so obtained for the different locations are stored into a repository 742 (action "A7.Truncate"); for example, each truncated array is defined by its first passage number $N_{fp}$ and a link to the associated data array 718 (so as to avoid duplicating the corresponding data).

The truncated arrays 742 are again supplied to the modeler 721. The modeler 721 now fits each truncated array 742 by an instance of the same simple bolus function $B_s(t)$, so as to obtain the corresponding truncated time-intensity function (being defined by the truncated fitting parameter values $O_t$, $A_t$, $m_t$ and $s_t$). The sets of truncated fitting parameter values $O_t$, $A_t$, $m_t$ and $s_t$ for the different locations are stored into a repository 745 (action "A8.Truncated fit").

An inizializer 748 accesses the repository 745 of the truncated fitting parameter values $O_t$, $A_t$, $m_t$ and $s_t$. For each location, the inizializer 748 initializes the fitting parameters $A_1$, $m_1$, $s_1$, $A_2$, $m_2$, $s_2$ and $\Delta t$ of the combined bolus function $B_c(t)$ for its fitting on the corresponding data array 718 (the fitting parameter $O_c$ is not initialized since it is assessed separately). For this purpose, each fitting parameter $A_1$, $A_2$ and $s_1$, $s_2$ is set to a multiple of the corresponding truncated fitting parameter value $A_t$ and $s_t$, respectively; for example, the fitting parameters $A_1$, $s_1$, $A_2$ and $s_2$ are set to:
$A_1 = A_t$,
$s_1 = s_t$,
$A_2 = 5 \cdot A_t$, and
$s_2 = 1.1 \cdot s_t$.

It should be noted that since the second bolus function $B_2(t)$ is completely independent of the first bolus function $B_1(t)$, the values of the fitting parameters $A_2$ and $s_2$ may significantly differ from the corresponding truncated fitting parameter values $A_t$ and $s_t$; therefore, the fitting parameters $A_2$ and $s_2$ are set to the corresponding truncated fitting parameter values $A_t$ and $s_t$ multiplied by a factor generally different from 1 (i.e., 5 and 1.1 in the example at issue).

Moreover, the inizializer 748 calculates the value of the mean transit time mTT for the truncated time-intensity function (referred to as truncated mean transit time value $mTT_t$):

$$mTT_t = e^{m_t + \frac{s_t^2}{2}}.$$

The truncated mean transit time value $mTT_t$ is used to set the mean transit time mTT for the first bolus function $B_1(t)$ and the second bolus function $B_2(t)$ of the combined bolus function $B_c(t)$ (denoted with $mTT_1$ and $mTT_2$, respectively) as above; for example, the mean transit times $mTT_1$ and $mTT_2$ are set to:
$mTT_1 = mTT_t$, and
$mTT_2 = 2 \cdot mTT_t$.

The initialization of the fitting parameters $m_1$ and $m_2$ is then obtained by calculating them from the initialization values of the mean transit times $mTT_1$ and $mTT_2$, respectively (in addition to the initialization values of the fitting parameters $s_1$ and $s_2$, respectively):

$$m_1 = \log(mTT_1) - \frac{s_1^2}{2} = \log(mTT_t) - \frac{s_t^2}{2}, \text{ and}$$

$$m_2 = \log(mTT_2) - \frac{s_2^2}{2} = \log(2 \cdot mTT_t) - \frac{(1.1 \cdot s_t)^2}{2}.$$

At the end, the fitting parameter $\Delta t$ as well is set to a multiple of the truncated mean transit time value $mTT_t$; for example, the fitting parameter $\Delta t$ is set to:
$\Delta t = 0.5 \cdot mTT_t$.

The sets of initialized fitting parameters of the combined bolus function $B_c(t)$ so obtained for the different locations are stored into a repository 751 (action "A9.Initialize").

At the same time, a constrainer 754 accesses the same repository 745 of the truncated fitting parameter values $O_t$, $A_t$, $m_t$ and $s_t$. For each location, the constrainer 754 calculates a set of constraints for the combined bolus function $B_c(t)$ (for its fitting on the corresponding data array 718). For this purpose, each fitting parameter $A_1$, $A_2$ and $s_1$, $s_2$ is constrained to vary (during the fitting operation) within a value range being defined by a lower limit and an upper limit that are set to multiples of the corresponding truncated fitting parameter value $A_t$ and $s_t$, respectively; for example, the fitting parameters $A_1$, $s_1$, $A_2$ and $s_2$ are constrained to vary within the value ranges:
$A_1$ = from $0.9 \cdot A_t$ to $1.25 \cdot A_t$,
$s_1$ = from $0.9 \cdot s_t$ to $1.25 \cdot s_t$,
$A_2$ = from 0 to $20 \cdot A_t$, and
$s_2$ = from 0 to $2 \cdot s_t$.

Likewise, the constrainer 754 calculates value ranges for each mean transit time $mTT_1$ and $mTT_2$, between a lower limit and an upper limit that are set to multiples of the truncated mean transit time value $mTT_t$; for example, the value ranges of the mean transit times $mTT_1$ and $mTT_2$ are set to:
$mTT_1$ = from $0.9 \cdot mTT_t$ to $1.25 \cdot mTT_t$, and
$mTT_2$ = from $mTT_t$ to $5 \cdot mTT_t$.

The constraints of the fitting parameters $m_1$ and $m_2$ are obtained as above from the value ranges of the mean transit times $mTT_1$ and $mTT_2$, respectively (in addition to the value ranges of the fitting parameters $s_1$ and $s_2$, respectively):

$$m_1 = \text{from } \log(0.9 \cdot mTT_t) - \frac{(0.9 \cdot s_t)^2}{2} \text{ to } \log(1.25 \cdot mTT_t) - \frac{(1.25 \cdot s_t)^2}{2},$$

and $$m_2 = \text{from } m_2 = \log(mTT_t) \text{ to } \log(5 \cdot mTT_t) - \frac{(2 \cdot s_t)^2}{2}.$$

Moreover, the fitting parameter $\Delta t$ as well is constrained to vary within a value range being defined by a lower limit and an upper limit that are set to multiples of the same truncated mean transit time value $mTT_t$; for example, the fitting parameter $\Delta t$ is constrained to vary within the value range:
$\Delta t$ = from 0 to $mTT_t$.

For example, an additional constraint is defined by forcing the mean transit time $mTT_2$ of the second bolus function $B_2(t)$ to be higher than the time to peak TP of the first bolus function $B_1(t)$ (denoted with $TP_1$):

$mTT_2 > TP_1$.

This additional constraint ensures that the second time-intensity function is always delayed with respect to the first time-intensity function.

The sets of constraints of the combined bolus function $B_c(t)$ so obtained for the different locations are stored into a repository 757 (action "A10.Constrain").

At this point, the modeler 721 fits each data array from the repository 718 by an instance of the combined bolus function $B_c(t)$, so as to obtain the corresponding combined time-intensity function (being defined by the values of its fitting parameters $O_c$, $A_1$, $m_1$, $s_1$, $A_2$, $m_2$, $s_2$ and $\Delta t$). For this purpose, the fitting parameters $A_1$, $m_1$, $s_1$, $A_2$, $m_2$, $s_2$ and $\Delta t$ are initialized as indicated in the repository 751, and they are constrained to vary (during the fitting operation) as indicated in the repository 757. The sets of fitting parameter values $O_c$, $A_1$, $m_1$, $s_1$, $A_2$, $m_2$, $s_2$ and $\Delta t$ so obtained for the different locations are stored into a repository 760 (action "A11.Combined fit").

Optionally, a differentiator 763 accesses both the repository 718 of the data arrays and the repository 760 of the fitting parameter values of the combined time-intensity functions. For each location, the differentiator 763 calculates a fitting array by evaluating the combined time-intensity function at every acquisition instant of the video images 706 (each one equal to a number of the corresponding video image 706 multiplied by the acquisition period); a difference array is then calculated by subtracting the fitting array from the data array 718 value by value. The difference arrays for the different locations are stored into a repository 766 (action "A12.Differentiate").

The modeler 721 then fits each difference array 766 by an instance of the simple bolus function $B_s(t)$, so as to obtain a third time-intensity function (being defined by the values of its fitting parameters $O_s$, $A_s$, $m_s$, and $s_s$, referred to as third fitting parameter values $O_3$, $A_3$, $m_3$, and $s_3$). The sets of third fitting parameter values so obtained for the different locations are stored into a repository 769 (action "A13.Difference fit"). These third time-intensity functions then represent a third passage of the contrast agent through the body-part (relating to a non-specific late phase thereof).

At this point, the sets of fitting parameter values 760 defining the combined time-intensity functions (including the sets of first fitting parameter values defining the first time-intensity functions and the sets of second fitting parameter values defining the second time-intensity functions that represent the first passage and the second passage, respectively, of the contrast agent through the corresponding locations of the body-part), and the possible sets of third fitting parameter values 769 defining the third time-intensity functions (that represent the third passage of the contrast agent through the same locations of the body-part) are supplied to a post-processor 772 (action "A14.Post-process"). For example, when the analysis process is performed at the level of pixels or groups of pixels, the post processor 772 generates a parametric image by assigning the value of a desired perfusion parameter to each pixel or group of pixel (which perfusion parameter values are calculated from one of the corresponding sets of first, second or third fitting parameter values); typically, the parametric image is color coded, by converting each perfusion parameter value into a discrete level (possibly applying a gain factor), and then associating it with the representation of a corresponding color (for example, by means of an index for accessing a location within a palette). For example, the parametric image is also superimposed on a selected one of the video images 706 (after restoring its full size by an interpolation operation when the parametric image has been calculated at the level of groups of pixels). Alternatively, when the analysis process is performed at the level of region of interest, the value of one or more perfusion parameters is calculated from one of the sets of first, second or third fitting parameter values. In any case, the information so obtained is used to characterize the corresponding locations of the body-part (for example, to detect and identify lesions of the body-part).

Modifications

Naturally, in order to satisfy local and specific requirements, a person skilled in the art may apply to the embodiments described above many logical and/or physical modifications and alterations. More specifically, although an embodiment may have been described with a certain degree of particularity, it should be understood that various omissions, substitutions and changes in the form and details as well as other embodiments are possible. Particularly, different embodiments may even be practiced without the specific details (such as the numerical examples) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment may be incorporated in any other embodiment as a matter of general design choice.

First of all, it should be noted that an embodiment of the proposed data-processing method may be implemented independently of any interaction with the patient (and particularly with the contrast agent that may be pre-administered thereto before performing the method). Moreover, the contrast agent may also be administered to the patient in a non invasive manner, or in any case without any substantial physical intervention thereon that would require professional medical expertise or entail any health risk for the patient. Although an embodiment of the proposed method facilitates the task of a physician, it generally only provides intermediate results that may help him/her in examining the body-part—for example, for diagnostic purposes (even though the diagnosis for curative purposes stricto sensu is always made by the physician himself/herself).

In any case, similar considerations apply if an embodiment is implemented with an equivalent data-processing method (by using similar steps with the same functions of more steps or portions thereof, removing some steps being non-essential, or adding further optional steps); moreover, the steps may be performed in a different order, concurrently or in an interleaved way (at least in part). For example, an embodiment of the proposed solution also lends itself to be put into practice with equivalent contrast agents; moreover, the contrast agent may be administered in an intra-arterial, intralymphatic, subcutaneous, intramuscular, intradermal, intraperitoneal, interstitial, intrathecal or intratumoral way, orally (for example, for imaging the gastro-intestinal tract), via a nebulizer into the airways, and the like. In any case, the possibility of applying an embodiment of the proposed solution to any other diagnostic systems—for example, based on Magnetic Resonance Imaging (MRI) or X-ray Computed Tomography (CT), is not excluded.

Moreover, nothing prevents applying an embodiment to 3-D video images (at the level of voxels, groups of voxels or 3-D region of interest); in any case, an embodiment may be applied either to a selected portion of the video images or to the whole extent thereof. The video images (or any equivalent input signals) to be processed according to an embodiment may be provided with any other technique. For example, one or more of the above-described pre-processing operations may be omitted, and/or the video images may be subject to alternative or different pre-processing operations—for example, by discarding unsuitable video images, realigning the video images, or filtering the echo signals digitally (such as by mean, median, or low-pass Butterworth filters); likewise, the resulting time-intensity functions may be subject to different and/or alternative post-processing operations (for example, by discarding the pixels that do not provide an acceptable level of quality of the fitting operation).

Moreover, one or more of the above-mentioned time-intensity functions may be used in any other way; for example, information relating to a vascular morphology of the body-part (e.g., a shunting being present in tumor tissue but absent in normal tissue) may be extracted from the second time-intensity functions. Moreover, the same information may also be used for representing an animated perfusion of the body-part (as described in WO-A-2006/108868, the entire disclosure of which is herein incorporated by reference). An embodiment may also be applied to any other parametric functions, with whatever kind and number of fitting parameters.

Moreover, nothing prevents using different parametric functions for the initial fitting on the echo signals (for determining the initial time-to-peak values), for fitting the truncated echo signals (for initializing the fitting parameters of the combined bolus function), and/or for fitting the difference data arrays (for determining the third time-intensity functions).

In any case, the possibility of using any other parametric function to model the second passage of the contrast agent is not excluded (even when the parametric function is not based on the sum of multiple simple bolus functions). Moreover, the combined bolus function may be based on the sum of three or more simple bolus functions (for corresponding secondary passages of the contrast agent through the body-part).

Alternative algorithms may be used during the different fitting operations. For example, during the fitting of each echo signal by the combined bolus function it is possible to assign lower weights to a first portion of the echo signal (for example, in the same truncation interval) and higher weights to a remaining portion thereof—so as to increase the relative contribution of the portion of the echo signal in which the second passage appears; particularly, when the fitting operation is based on the above-mentioned gradient descent algorithm, the difference between the current instance of the combined bolus function and the echo signal (being used to determine the direction of the lowest gradient) may be based on a weighted sum of the instantaneous squared differences between each value of the time-intensity function and the corresponding echo power value according to their weights. Moreover, the proposed procedure may be reiterated by using the fitting parameter values of the combined time-intensity function to initialize the combined bolus function again for a further fitting thereof on the same echo signal. Nothing prevents initializing the fitting parameters of the combined bolus function according to whatever combination of values being derived from the corresponding initial time-intensity function (in addition or in alternative to the truncated mean transit time value).

Particularly, the delay of each second bolus function may be initialized in any other way—for example, according to the corresponding initial time-to-peak value.

Moreover, the delay of each second bolus function may be initialized to a different multiple of the truncated mean transit time value (even equal to or higher than 1).

The mean transit time values of the first and second bolus functions may be calculated in another way from the truncated mean transit time value (for initializing one or more of their fitting parameters in whatever way according to the corresponding values calculated therefrom).

For example, the mean transit time values of the first and second bolus functions may be set to the truncated mean transit time value multiplied by different factors.

Similar considerations apply to other simple bolus functions (for example, lagged lognormal, gamma variate, local density random walk, and so on).

Likewise, one or more fitting parameters of the first and second bolus functions may be initialized to the corresponding truncated parameter values multiplied by different factors (either equal to or different from 1).

The fitting parameters of the combined bolus function may be constrained in any other way (even if this step is not strictly necessary).

Similar considerations apply if the mean of the combined bolus function is initialized and/or constrained according to the value of the same fitting parameter of the corresponding truncated time-intensity function, or vice-versa if other fitting parameters are initialized and/or constrained according to the corresponding truncated mean transit time value.

Moreover, it is possible to constrain the fitting parameters of the combined bolus function according to different multiples of the corresponding truncated fitting parameter values; for example, the constraint of each fitting parameter of the combined bolus function may be expressed as a percentage of allowed variation around its initialization value. In a different embodiment, it is also possible to apply this kind of constraining to all the fitting parameters of the combined bolus function.

Similar considerations apply to the constraining based on the mean transit time values of the first and second bolus functions.

Moreover, the mean transit time of the second bolus function may be constrained to exceed any other function of the time to peak of the first bolus function (even if this additional constraint may be omitted in a simplified implementation).

Similar considerations apply to the fitting parameters of the first and/or second bolus function that are initialized according to the corresponding truncated fitting parameter values.

The above-described solution lends itself to be implemented by estimating the peak instant of each echo signal in a different way; for example, it is possible to filter each echo signal by applying a Maximum Intensity Projection (MIP) algorithm (which holds the echo signal at its maximum over time), and then monitoring the filtered echo signal so obtained to detect its peak instant as soon as the filtered echo signal remains constant for a predefined stability time-window (as described in WO-A-2010/058014, the entire disclosure of which is herein incorporated by reference).

Naturally, the differentiation between the echo signals and the corresponding combined time-intensity functions (for determining the third time-intensity functions) is merely optional.

Each truncation interval may be determined in any other way (for example, by taking into account further values being derived from the initial time-intensity function in addition to the initial time-to-peak value); moreover, it is also possible to set the start of the truncation interval to an arrival instant, which is determined as the instant at which the echo signal exceeds a predefined threshold value. In any case, the above-described numerical examples of the factor to be applied to the initial time-to-peak values for obtaining the first passage times are merely illustrative.

An embodiment may be implemented as a stand-alone module, as a plug-in for a control program of the ultrasound scanner, or even directly in the control program itself; it would be readily apparent that it is also possible to deploy an embodiment as a service that is accessed through a network (such as in the Internet). Similar considerations apply if the program (which may be used to implement each embodiment) is structured in a different way, or if additional modules or functions are provided; likewise, the memory structures may be of other types, or may be replaced with equivalent entities (not necessarily consisting of physical storage media). In any case, the program may take any form suitable to be used by any data-processing system or in connection therewith (for example, within a virtual machine); particularly, the program may be in the form of external or resident software, firmware, or microcode (either in object code or in source code—for example, to be compiled or interpreted). Moreover, it is possible to provide the program on any computer-usable medium; the medium may be any element suitable to contain, store, communicate, propagate, or transfer the program. For example, the medium may be of the electronic, magnetic, optical, electromagnetic, infrared, or semiconductor type; examples of such medium are fixed disks (where the program can be pre-loaded), removable disks, tapes, cards, wires, fibers, wireless connections, networks, broadcast waves, and the like. In any case, an embodiment lends itself to be implemented even with a hardware structure (for example, integrated in a chip of semiconductor material), or with a combination of software and hardware.

Similar considerations apply if the ultrasound scanner has a different structure or includes equivalent components, or it has other operative characteristics (for example, with an imaging probe of the linear-, convex-, phased-, or matrix-array type). In any case, every component thereof may be separated into more elements, or two or more components may be combined together into a single element; moreover, each component may be replicated to support the execution of the corresponding operations in parallel. It is also pointed out that (unless specified otherwise) any interaction between different components generally does not need to be continuous, and it may be either direct or indirect through one or more intermediaries. Alternatively, an embodiment may be applied in a diagnostic system including an ultrasound scanner and a distinct computer (or any equivalent data-processing system); in this case, the recorded information is transferred from the ultrasound scanner to the computer for its processing (for example, through a digital, analogue or network connection).

The above-described embodiments, as well as any modification thereof, may advantageously be used in a conventional diagnostic method. More generally, an embodiment may find application in any kind of diagnostic applications (in the broadest meaning of the term—for example, aimed at either discovering new lesions or monitoring known lesions) and for analyzing any kind of body-parts (for example, liver, prostate, heart, and so on).

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated An embodiment is proposed for analyzing a body-part perfused with a contrast agent, which has been pre-administered as a bolus to circulate through the body-part with a first passage and possibly with at least one second passage during an analysis interval. A corresponding data-processing method includes the steps of providing at least one input signal indicative of a response to an interrogation signal of a corresponding location of the body-part during the analysis interval, and fitting each input signal over the analysis interval by an instance of a combined bolus function of time, based on a combination of a first simple bolus function of time modeling the first passage of the contrast agent and at least one second simple bolus function of time each one modeling a corresponding second passage of the contrast agent, being defined by the values of a set of first fitting parameters of the first simple bolus function, a set of second fitting parameters of each second simple bolus function and a delay parameter of each second simple bolus function with respect to the first simple bolus function. In an embodiment, the step of fitting each input signal includes estimating a peak instant of the input signal when the corresponding response reaches an absolute peak, setting a truncation interval within the analysis interval according to the peak instant, fitting a truncated signal defined by the input signal over the truncation interval by an instance of a truncated simple bolus function of time, modeling a single passage of the contrast agent during the truncation interval, being defined by the values of a set of truncated fitting parameters, and initializing the first fitting parameters, the second fitting parameters of each second simple bolus function and the delay parameter of each second simple bolus function according to the values of the truncated fitting parameters.

The invention claimed is:

1. A data-processing method for analyzing a body-part perfused with an ultrasound contrast agent, the ultrasound contrast agent being pre-administered as a bolus to circulate through the body-part with a first passage and with at least one second passage during an analysis interval, wherein the method includes the steps of:
   displaying one or more video images of the body-part on a monitor of a data-processing system,
   storing a representation of at least one input signal indicative of a response to an ultrasound interrogation signal of a corresponding location of the body-part during the analysis interval in a memory of the data-processing system,
   fitting, by the data-processing system accordingly configured, each input signal over the analysis interval by an instance of a combined bolus function of time, based on a combination of a first bolus function of time modeling the first passage of the contrast agent and at least one second bolus function of time each one modeling a corresponding second passage of the ultrasound contrast agent, being defined by the values of a set of first fitting parameters of the first bolus function, a set of second fitting parameters of each second bolus function and a delay parameter of each second bolus function with respect to the first bolus function,
   generating a parametric image of the body-part based on each combined bolus function of time, and superimposing the parametric image on a selected video image on the monitor of the data-processing system for use in analyzing the body-part,
wherein
the step of fitting each input signal includes:
estimating a peak instant of the input signal when the corresponding response reaches an absolute peak,
setting a truncation interval within the analysis interval according to the peak instant,
fitting a truncated signal defined by the input signal over the truncation interval by an instance of a truncated bolus function of time, modeling a single passage of the contrast agent during the truncation interval, being defined by the values of a set of truncated fitting parameters, and
initializing the first fitting parameters, the second fitting parameters of each second bolus function and the delay parameter of each second bolus function according to the values of the truncated fitting parameters.

2. The method according to claim 1, wherein the step of fitting each input signal further includes:
calculating the value of a truncated mean transit time of the truncated bolus function, and
initializing at least one fitting parameter among the first fitting parameters, the second fitting parameters of each second bolus function and the delay parameter of each second bolus function according to the value of the truncated mean transit time.

3. The method according to claim 2, wherein the step of initializing at least one fitting parameter includes:
initializing the delay parameter of each second bolus function to a fraction of the value of the truncated mean transit time.

4. The method according to claim 2, wherein the step of initializing at least one fitting parameter, includes:
calculating the value of a first mean transit time for the first bolus function and the value of a second mean transit time for each second bolus function according to the value of the truncated mean transit time, and
initializing at least one of the first fitting parameters to the corresponding value calculated from the value of the first mean transit time, and at least one of the second fitting parameters of each second bolus function to the corresponding value calculated from the value of the second mean transit time.

5. The method according to claim 4, wherein the step of initializing at least one of the first fitting parameters and at least one of the second fitting parameters includes:
setting the value of the first mean transit time to the value of the truncated mean transit time multiplied by a first setting factor, and setting the value of the second mean transit time for each second bolus function to the value of the truncated mean transit time multiplied by a second setting factor.

6. The method according to claim 4, wherein the first bolus function and each second bolus function are lognormal distribution functions, said at least one of the first fitting parameters and said at least one of the second fitting parameters including a mean and a standard deviation of a distribution of the natural logarithm of time of the first bolus function and the second bolus function, respectively.

7. The method according to claim 4, wherein the step of fitting each input signal further includes:
constraining the first fitting parameters, the second fitting parameters of each second bolus function and the delay parameter of each second bolus function according to the values of the truncated fitting parameters;
wherein the step of constraining includes:
constraining said at least one fitting parameter according to the value of the truncated mean transit time; and
wherein the step of constraining further includes:
calculating a lower first mean transit time limit and an upper first mean transit time limit for the first bolus function equal to the value of the truncated mean transit time multiplied by a lower first constraining factor and an upper first constraining factor, respectively, and a lower second mean transit time limit and an upper second mean transit time limit for each second bolus function equal to the value of the truncated mean transit time multiplied by a lower second constraining factor and an upper second constraining factor, respectively, and
constraining said at least one of the first fitting parameters to range between a corresponding lower first limit and a corresponding upper first limit calculated from the lower first mean transit time limit and the upper first mean transit time limit, respectively, and constraining said at least one of the second fitting parameters to range between a corresponding lower second limit and a corresponding upper second limit calculated from the lower second mean transit time limit and the upper second mean transit time limit, respectively.

8. The method according to claim 2, wherein the step of fitting each input signal further includes:
constraining the first fitting parameters, the second fitting parameters of each second bolus function and the delay parameter of each second bolus function according to the values of the truncated fitting parameters; and
wherein the step of constraining includes:
constraining said at least one fitting parameter according to the value of the truncated mean transit time.

9. The method according to claim 8, wherein the step of constraining includes:
constraining the delay parameter of each second bolus function to range between a lower delay limit and an upper delay limit, the lower delay limit and the upper delay limit being equal to the value of the truncated mean transit time multiplied by a lower delay constraining factor and an upper delay constraining factor, respectively.

10. The method according to claim 1, wherein the step of initializing includes:
initializing at least one of the second fitting parameters of each second bolus function to the value of the corresponding truncated fitting parameter multiplied by an initialization factor different from 1.

11. The method according to claim 1, wherein the step of fitting each input signal further includes:
constraining the first fitting parameters, the second fitting parameters of each second bolus function and the delay parameter of each second bolus function according to the values of the truncated fitting parameters.

12. The method according to claim 11, wherein the step of constraining includes:
constraining a second mean transit time of each second bolus function to exceed a first time to peak of the first bolus function.

13. The method according to claim 11, wherein the step of constraining includes:
constraining at least one of the first fitting parameters to range between a lower further first limit and an upper further first limit equal to the value of the corresponding truncated parameter multiplied by a lower further first constraining factor and an upper further first constraining factor, respectively, and at least one of the second fitting parameters of each second bolus function to range between a lower further second limit and an upper further second limit equal to the value of the corresponding truncated parameter multiplied by a lower further second constraining factor and an upper further second constraining factor, respectively.

14. The method according to claim 1, wherein the step for estimating a peak instant includes:
   fitting the input signal over the analysis interval by an instance of an initial bolus function of time modeling a single passage of the contrast agent during the analysis interval, and
   calculating the peak instant from the initial bolus function.

15. The method according to claim 1, further including the steps of:
   calculating a difference signal from each input signal by subtracting the values of the corresponding combined bolus function at corresponding instants from the input signal, and
   fitting each difference signal by a third bolus function of time modeling a third passage of the contrast agent.

16. The method according to claim 1, wherein the step of setting a truncation interval includes:
   setting an end of the truncation interval equal to the peak instant multiplied by a truncation factor.

17. A diagnostic method for analyzing a body-part, the diagnostic method including the steps of:
   administering an ultrasound contrast agent to the body-part to cause the body-part to be perfused with the ultrasound contrast agent, the ultrasound contrast agent being administered as a bolus to circulate through the body-part with a first passage and with at least one second passage during an analysis interval,
   applying an ultrasound interrogation signal to the body-part during the analysis interval,
   acquiring at least one input signal indicative of a response to the ultrasound interrogation signal of a corresponding location of the body-part during the analysis interval, each input signal being processed according to the data-processing method of claim 1 to obtain the corresponding combined bolus function, and
   assessing a perfusion of each location of the body-part according to the corresponding combined bolus function.

18. A data-processing system including an electronic circuit configured to perform the steps of a data-processing method for analyzing a body-part perfused with an ultrasound contrast agent, the ultrasound contrast agent being pre-administered as a bolus to circulate through the body-part with a first passage and with at least one second passage during an analysis interval, wherein the data-processing method includes the steps of:
   displaying one or more video images of the body-part on a monitor of the data-processing system,
   storing a representation of at least one input signal indicative of a response to an ultrasound interrogation signal of a corresponding location of the body-part during the analysis interval in a memory of the data-processing system,
   fitting, by the data-processing system, each input signal over the analysis interval by an instance of a combined bolus function of time, based on a combination of a first bolus function of time modeling the first passage of the ultrasound contrast agent and at least one second bolus function of time each one modeling a corresponding second passage of the ultrasound contrast agent, being defined by the values of a set of first fitting parameters of the first bolus function, a set of second fitting parameters of each second bolus function and a delay parameter of each second bolus function with respect to the first bolus function,
   generating a parametric image based on each combined bolus function of time, and
   superimposing the parametric image on a selected video image of the body-part on the monitor of the data-processing system for use in analyzing the body-part,
   wherein
   the step of fitting each input signal includes:
      estimating a peak instant of the input signal when the corresponding response reaches an absolute peak,
      setting a truncation interval within the analysis interval according to the peak instant,
      fitting a truncated signal defined by the input signal over the truncation interval by an instance of a truncated bolus function of time, modeling a single passage of the ultrasound contrast agent during the truncation interval, being defined by the values of a set of truncated fitting parameters, and
      initializing the first fitting parameters, the second fitting parameters of each second bolus function and the delay parameter of each second bolus function according to the values of the truncated fitting parameters.

19. A non-transitory computer readable medium storing program instructions that are directly loadable into a working memory of a data-processing system, and that, when executed by the data-processing system, cause the data-processing system to perform a data-processing method for analyzing a body-part perfused with an ultrasound contrast agent, the ultrasound contrast agent being pre-administered as a bolus to circulate through the body-part with a first passage and with at least one second passage during an analysis interval, wherein the data-processing method includes the steps of:
   displaying one or more video images of the body-part on a monitor of the data-processing system,
   storing a representation of at least one input signal indicative of a response to an ultrasound interrogation signal of a corresponding location of the body-part during the analysis interval in a memory of the data-processing system,
   fitting, by the data-processing system, each input signal over the analysis interval by an instance of a combined bolus function of time, based on a combination of a first bolus function of time modeling the first passage of the ultrasound contrast agent and at least one second bolus function of time each one modeling a corresponding second passage of the ultrasound contrast agent, being defined by the values of a set of first fitting parameters of the first bolus function, a set of second fitting parameters of each second bolus function and a delay parameter of each second bolus function with respect to the first bolus function, generating a parametric image based on each combined bolus function of time, and
   superimposing the parametric image on a selected video image of the body-part on the monitor of the data-processing system for use in analyzing the body-part,
   the step of fitting each input signal including:
      estimating a peak instant of the input signal when the corresponding response reaches an absolute peak, setting a truncation interval within the analysis interval according to the peak instant, fitting a truncated signal defined by the input signal over the truncation interval by an instance of a truncated bolus function of time, modeling a single passage of the contrast agent during the truncation interval, being defined by the values of a set of truncated fitting parameters, and initializing the first fitting parameters, the second fitting parameters of each second bolus function and the delay parameter of each second bolus function for the fitting of the input signal by the combined bolus function according to the values of the truncated fitting parameters.

* * * * *